(12) United States Patent
Rowe

(10) Patent No.: US 11,872,152 B2
(45) Date of Patent: Jan. 16, 2024

(54) APPENDAGE PRESSURIZATION DEVICES COMPRISING ARTIFICIAL MUSCLES

(71) Applicant: Toyota Motor Engineering & Manufacturing North America, Inc., Plano, TX (US)

(72) Inventor: Michael P. Rowe, Pinckney, MI (US)

(73) Assignee: Toyota Motor Engineering & Manufacturing North America, Inc., Plano, TX (US)

( * ) Notice: Subject to any disclaimer, the term of this patent is extended or adjusted under 35 U.S.C. 154(b) by 482 days.

(21) Appl. No.: 16/931,608

(22) Filed: Jul. 17, 2020

(65) Prior Publication Data
US 2022/0015933 A1  Jan. 20, 2022

(51) Int. Cl.
*A61F 5/01* (2006.01)
*A61F 5/34* (2006.01)
*A61F 2/70* (2006.01)

(52) U.S. Cl.
CPC ............ *A61F 5/012* (2013.01); *A61F 2/70* (2013.01); *A61F 5/34* (2013.01); *A61F 2005/0155* (2013.01); *A61F 2005/0188* (2013.01)

(58) Field of Classification Search
CPC ...... A61F 5/0102; A61F 5/05816; A61F 5/32; A61F 5/34; A61F 5/012; A61F 2005/0188; A61F 2005/0155; A61F 2/70
(Continued)

(56) References Cited

U.S. PATENT DOCUMENTS 7,679,261 B2   3/2010  Chappaz et al.
7,834,527 B2  11/2010  Alvarez et al.
(Continued)

FOREIGN PATENT DOCUMENTS

CN   104942791 A   9/2015
CN   109806548 A   5/2019
(Continued)

OTHER PUBLICATIONS

Shane Mitchell, et al., "An Easy-To-Implement Toolkit To Create Versatile And High-Performance HASEL Actuators For Untethered Soft Robots," Journal Article, Advanced Science 6(14):1900178, Jun. 2019, URL: https://www.researchgate.net/figure/Generalized-principle-of-zipping-mode-actuation-in-HASEL-actuators-As-voltage-is_fig1_333725822, 15 pages.
(Continued)

*Primary Examiner* — Ophelia A Hawthorne
*Assistant Examiner* — Michael Milo
(74) *Attorney, Agent, or Firm* — Dinsmore & Shohl LLP

(57) ABSTRACT

An appendage pressurization device includes an appendage strap and one or more artificial muscles communicatively coupled to a controller. Each artificial muscle includes a housing having an electrode region, an expandable fluid region, a dielectric fluid housed within the housing, and an electrode pair positioned in the electrode region of the housing. The electrode pair includes a first electrode fixed to a first surface of the housing and a second electrode fixed to a second surface of the housing, wherein the electrode pair is actuatable between a non-actuated state and an actuated state. Actuation from the non-actuated state to the actuated state directs the dielectric fluid into the expandable fluid region. A pressure sensor is communicatively coupled to the controller, wherein the pressure sensor outputs a current
(Continued)

pressure value to the controller and actuation of the electrode pair is based on the current pressure value.

19 Claims, 13 Drawing Sheets

(58) Field of Classification Search
USPC .................. 602/13; 601/149, 150, 151, 152
See application file for complete search history.

(56) References Cited

U.S. PATENT DOCUMENTS

| | | | |
|---|---|---|---|
| 7,857,777 B2* | 12/2010 | Larson | A61H 7/00 |
| | | | 602/61 |
| 10,233,910 B2 | 3/2019 | Mazzeo et al. | |
| 2010/0268092 A1 | 10/2010 | Kobayashi et al. | |
| 2012/0101598 A1* | 4/2012 | Altobelli | A61F 5/012 |
| | | | 211/13.1 |
| 2014/0101862 A1* | 4/2014 | Misaki | A61G 7/05738 |
| | | | 5/710 |
| 2014/0277739 A1* | 9/2014 | Kornbluh | F16D 28/00 |
| | | | 29/428 |
| 2014/0373594 A1* | 12/2014 | Remez | G01L 1/146 |
| | | | 73/1.08 |
| 2017/0181882 A1* | 6/2017 | Chisena | A61F 5/30 |
| 2019/0000329 A1* | 1/2019 | Denson | A61B 5/7246 |
| 2020/0032822 A1* | 1/2020 | Keplinger | F15B 21/065 |
| 2021/0172460 A1* | 6/2021 | Keplinger | F15B 15/103 |
| 2021/0284525 A1* | 9/2021 | Liu | F04B 43/14 |
| 2022/0158570 A1* | 5/2022 | Keplinger | B32B 27/08 |

FOREIGN PATENT DOCUMENTS

| | | |
|---|---|---|
| CN | 209812321 U | 12/2019 |
| DE | 102015212586 B3 * | 1/2017 |
| JP | 2007097292 A | 4/2007 |
| JP | 2014228017 A | 12/2014 |
| WO | 2012016792 A1 | 2/2012 |
| WO | 2019002860 A1 | 1/2019 |
| WO | 2019173227 A1 | 9/2019 |

OTHER PUBLICATIONS

Nasrul Anuar Abd Razak, et al., "Prosthetics Socket That Incorporates An Air Splint System Focusing On Dynamic Interface Pressure," Journal Article, Biomedical Engineering Online, Aug. 1, 2014, vol. 13, Department of Biomedical Engineering, Faculty of Engineering, University of Malaya, 50603 Kuala Lumpur, Malaysia.

E. Acome, et al., "Hydraulically Amplified Self-Healing Electrostatic Actuators With Muscle-Like Performance," Science Journal, Jan. 5, 2018: vol. 359, Issue 6371, pp. 61-651, Department of Mechanical Engineering & Materials Science and Engineering Program, University of Colorado, Boulder, CO 80309, USA.

* cited by examiner

APPENDAGE PRESSURIZATION DEVICES COMPRISING ARTIFICIAL MUSCLES

TECHNICAL FIELD

The present specification generally relates appendage pressurization devices and, in particular, to appendage pressurization devices that include artificial muscles for providing a consistent amount of pressure to a user.

BACKGROUND

Medical devices are typically strapped to a patient's arm, leg, hand, foot, etc. by means of a cuff (nylon, etc.) that is kept in place by making it overly tight and held with Velcro. These cuffs must be both secure and comfortable, but this can be an engineering challenge because people move, flex, shift, and are soft. This makes it difficult for the patient to receive consistent, comfortable pressure from the cuff in a way that also consistently holds the cuff securely to the patient.

Accordingly, there is a need exists for improved pressurization devices that are low profile while able to apply a consistent amount of pressure to a user.

SUMMARY

In one embodiment, an appendage pressurization device includes an appendage strap and one or more artificial muscles disposed in the appendage strap and communicatively coupled to a controller. Each artificial muscle includes a housing comprising an electrode region and an expandable fluid region, a dielectric fluid housed within the housing, and an electrode pair positioned in the electrode region of the housing, the electrode pair comprising a first electrode fixed to a first surface of the housing and a second electrode fixed to a second surface of the housing, wherein the electrode pair is actuatable between a non-actuated state and an actuated state such that actuation from the non-actuated state to the actuated state directs the dielectric fluid into the expandable fluid region, expanding the expandable fluid region. The appendage pressurization device also includes a pressure sensor communicatively coupled to the controller, wherein the pressure sensor is configured to output a current pressure value to the controller and actuation of the electrode pair is based on the current pressure value.

In another embodiment, a method for actuating an appendage pressurization device includes generating a voltage using a power supply electrically coupled to an electrode pair of an artificial muscle. The artificial muscle may be disposed in an appendage strap. The artificial muscle includes a housing having an electrode region and an expandable fluid region. The electrode pair is positioned in the electrode region of the housing. The electrode pair includes a first electrode fixed to a first surface of the housing and a second electrode fixed to a second surface of the housing. A dielectric fluid is housed within the housing. A pressure sensor is affixed to the housing and communicatively coupled to a controller. The method also includes applying the voltage to the electrode pair of the artificial muscle, thereby actuating the electrode pair from a non-actuated state to an actuated state such that the dielectric fluid is directed into the expandable fluid region of the housing and expands the expandable fluid region, thereby applying pressure to the inner layer of the appendage strap. The method further includes outputting, via the pressure sensor, a pressure value to the controller. The method additionally includes receiving, from the controller, an updated pressure value at the artificial muscle to maintain a consistent amount of pressure at the inner layer of the appendage strap based upon the pressure value. The method also includes adjusting the actuation of the artificial muscle to maintain the consistent amount of pressure at the inner layer of the appendage strap.

In yet another embodiment, an appendage pressurization device includes a an appendage brace, an appendage strap coupled to the appendage brace, and a plurality of the artificial muscles are disposed in the appendage strap and communicatively coupled to a controller. Each artificial muscle comprises a housing comprising an electrode region and an expandable fluid region, a dielectric fluid housed within the housing, and an electrode pair positioned in the electrode region of the housing, the electrode pair comprising a first electrode fixed to a first surface of the housing and a second electrode fixed to a second surface of the housing, wherein the electrode pair is actuatable between a non-actuated state and an actuated state such that actuation from the non-actuated state to the actuated state directs the dielectric fluid into the expandable fluid region, thereby expanding the expandable fluid region. A pressure sensor is communicatively coupled to the controller, wherein the pressure sensor is configured to output a current pressure value to the controller. The controller is configured to receive a current pressure value from one the pressure sensor, output an updated pressure value to artificial muscles, wherein a consistent amount of pressure at an inner layer of the appendage strap is maintained based upon a feedback loop maintained by the controller in coordination with the one or more pressure sensors, and modify actuation of plurality of artificial muscles based upon the updated pressure value.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

Figure 1A:
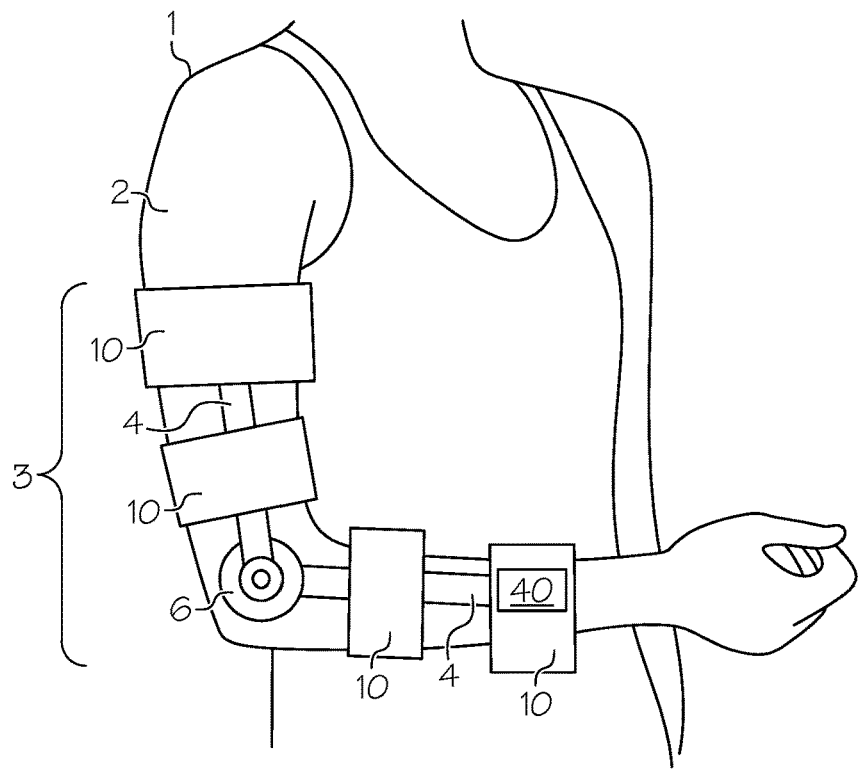
FIG. 1A schematically depicts an appendage pressurization device positioned on the arm of a user, according to one or more embodiments shown and described herein.
Figure 1B:
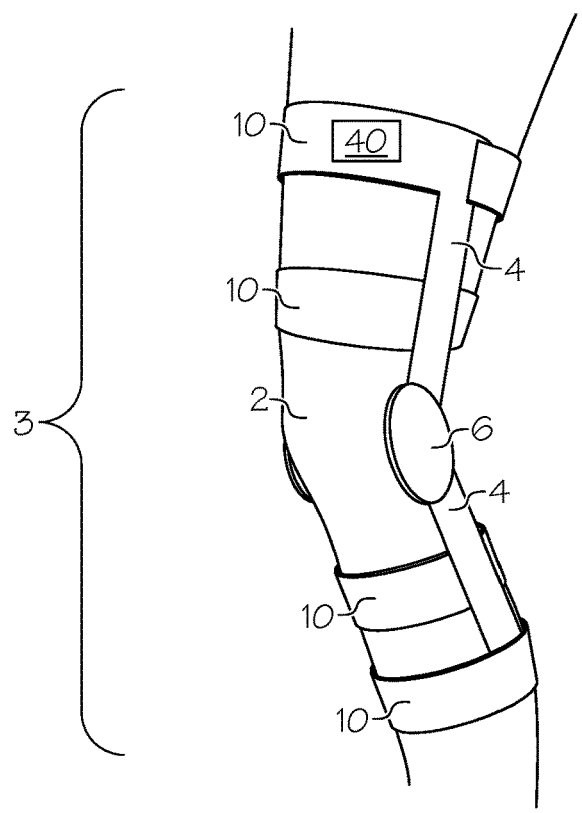
FIG. 1B schematically depicts an appendage pressurization device positioned on the leg of a user, according to one or more embodiments shown and described herein.
Figure 1C:
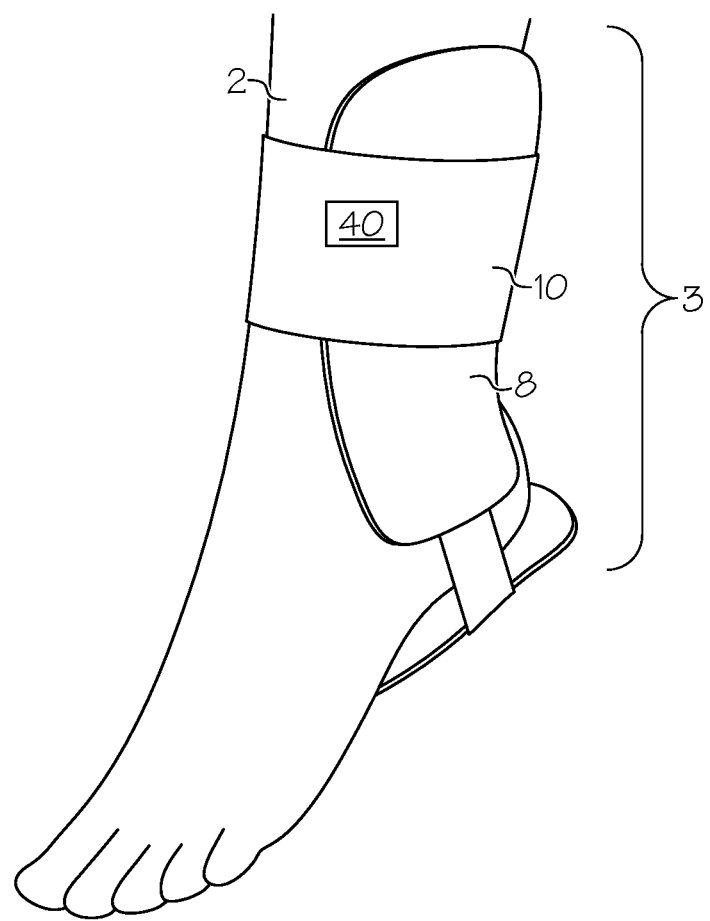
FIG. 1C schematically depicts an appendage pressurization device positioned on the ankle of a user, according to one or more embodiments shown and described herein.

Embodiments described herein are directed to appendage pressurization devices that include one or more artificial muscles configured to apply a selective pressure to an appendage of a user. The appendage pressurization devices described herein include an appendage brace, such as a knee brace, ankle brace, back brace, elbow brace, or the like, having at least one appendage strap having an appendage opening with a dynamic radius facilitated by one or more artificial muscles. The appendage strap includes an inner layer, an outer layer, and one or more artificial muscles disposed in a cavity between the inner layer and the outer layer that are actuatable to selectively raise and lower a region of the artificial muscles to provide a selective, on demand inflated expandable fluid region. In particular, the one or more artificial muscles each include an electrode pair that may be drawn together by application of a voltage, thereby pushing dielectric fluid into the expandable fluid region, which applies localized pressure to the inner layer of the appendage strap. Actuation of the one or more artificial muscles of the appendage pressurization device may dynamically alter the inner diameter of the appendage strap by applying selective and customizable pressure such that the appendage strap applies a consistent pressure to the user to hold the orthopedic brace on the appendage of the user as the user moves. Various embodiments of the appendage pressurization device and the operation of the appendage pressurization device are described in more detail herein. Whenever possible, the same reference numerals will be used throughout the drawings to refer to the same or like parts.

Referring now to FIGS. 1A-2D, an appendage pressurization device 10 is schematically depicted. In FIG. 1A-1C, embodiments of the appendage pressurization device 10 are depicted disposed on an appendage 2 of a user 1, such as an arm (FIG. 1A), a leg (FIG. 1B), and an ankle (FIG. 1C). The appendage pressurization devices 10 are used to hold an appendage brace 3 in place on a user's appendage 2. The appendage brace 3 may be used to control, guide, limit, and/or immobile a joint or body segment of the user 1, such as a limb (e.g., appendage 2), joint, or back of the user 1. For example, the appendage brace 3 may restrict movement of the joint or body segment in a particular direction and reduce weight bearing on the joint or body segment. Example implementations of the appendage brace 3 include aiding rehabilitation of the joint or body segment, such as rehabilitation from fractures, correcting the shape or function or the joint or body segment, facilitating easier movement capabilities, and reducing pain. The appendage brace 3 may have connectors 4 which may be utilized to maintain physical, electrical, and/or data connections between multiple appendage pressurization devices 10. The appendage brace 3 may have also feature one or more joints 6, which may be utilized to connect multiple connectors 4 in order to allow a user to maintain the freedom to bend an appendage, such as at the elbow or knee.

Referring still to FIGS. 1A-2D, the appendage pressurization device 10 includes one or more appendage straps 12. The appendage strap 12 includes an outer layer 20, an inner layer 30, a cavity 15 disposed between the outer layer 20 and the inner layer 30, and an appendage opening 25. The appendage strap 12 may be utilized to hold the appendage brace 3 in place on the user 1, and thereby the constituent connectors 4 and joint 6 as well. The appendage pressurization device 10 also includes one or more artificial muscles 101 disposed between the inner layer 30 and the outer layer 20 of the appendage strap 12, for example, in the cavity 15. As described herein, selective actuation of the one or more artificial muscles 101 may be used to dynamically alter the radius of the appendage opening 25 of each appendage strap 12 to hold the appendage brace 3 on the user 1 with consistent pressure, for example, when the user 1 is moving the appendage 2 or other body segment on which the appendage brace 3 is disposed.

In FIGS. 2A-2D, a schematic cross-section of the appendage pressurization device 10 is shown in various states of actuation. In the embodiments depicted in FIGS. 2A-2D, each artificial muscle 101 is one of a plurality of artificial muscles 100. In particular, the plurality of artificial muscles 100 in FIGS. 2A-2D are arranged in a plurality of artificial muscle stacks 102. Moreover, embodiments are contemplated with a plurality of artificial muscles 100 arranged in a single layer within the cavity 15, in contrast to the artificial muscle stacks 102 of FIG. 2A-2D. In operation, the one or more artificial muscles 101 are actuatable to expand and apply a pressure to the inner layer 30 of the appendage strap 12. When the appendage strap 12 is worn, pressure induced by each artificial muscles 101 may hold the appendage brace 3 on the user 1 in a consistent manner (e.g., by maintaining consistent pressure between the appendage 2 and the appendage strap 12) as the user 1 moves. That is, maintaining consistent pressure at the inner layer 30 of the appendage strap 12. For example, as the user 1 bends their knee, less pressure will be needed by the appendage strap 12 because the leg will flex and thus actuation of the plurality of artificial muscles 100 may be reduced to increase the radius of the appendage opening 25 of the appendage strap 12 and maintain constant pressure on the leg. Then, as the user 1 straightens their knee, the leg relaxes and thus actuation of the plurality of artificial muscles 100 may be increased to reduce the radius of the appendage opening 25 of the appendage strap 12 and maintain constant pressure on the leg. Moreover, as body segments, such as appendages 2, are not simple and uniform shapes, actuation of each artificial muscle 101 of the plurality of artificial muscles 100 may be independent and selective to maintain consistent pressure on the user 1. In other words, local radii of the appendage opening 25 may be selectively and independently altered by the plurality of artificial muscles 100. In operation, actuation of the one or more artificial muscles 101 may be controlled by an actuation system 400, which, as described in more detail with respect to FIG. 10, may include components housed in an onboard control unit 40 coupled to the appendage strap 12. This may include, for example, utilizing a pressure value (Pa/pascal, PSI, etc.) to determine the actuation amount of the one or more artificial muscles 101.

The inner layer 30 comprises an inner surface 32 facing the cavity 15 and an outer surface 34 facing an appendage opening 25. The inner surface 32 may contact at least one artificial muscle 101 and, when worn, the outer surface 34 may contact the appendage 2 of the user 1. The outer layer 20 comprises an inner surface 22 facing the cavity 15 and an outer surface 24 facing outward from the appendage strap 12. The inner surface 22 of the outer layer 20 may contact at least one artificial muscle 101. The inner layer 30 comprises an elastic material such that, when worn, the inner layer 30 may conform to the contours of the appendage 2 of the user 1. In one embodiment, the outer layer 20 comprises a more rigid material than the inner layer 30, such as a rigid plastic or polymeric material, such that when the one or more artificial muscles 101 are actuated and press against both the inner layer 30 and the outer layer 20, the inner layer 30 deforms a greater degree than the outer layer 20 (indeed, the outer layer 20 may not deform at all) such that pressure is applied to the appendage 2 of the user 1. As the outer layer 20 is more rigid than the inner layer 30, the outer layer 20 comprises a higher Young's modulus than the inner layer 30. In other embodiments, the outer layer 20 utilizes a less or equally rigid material in comparison to the inner layer 30.

Figure 2A:
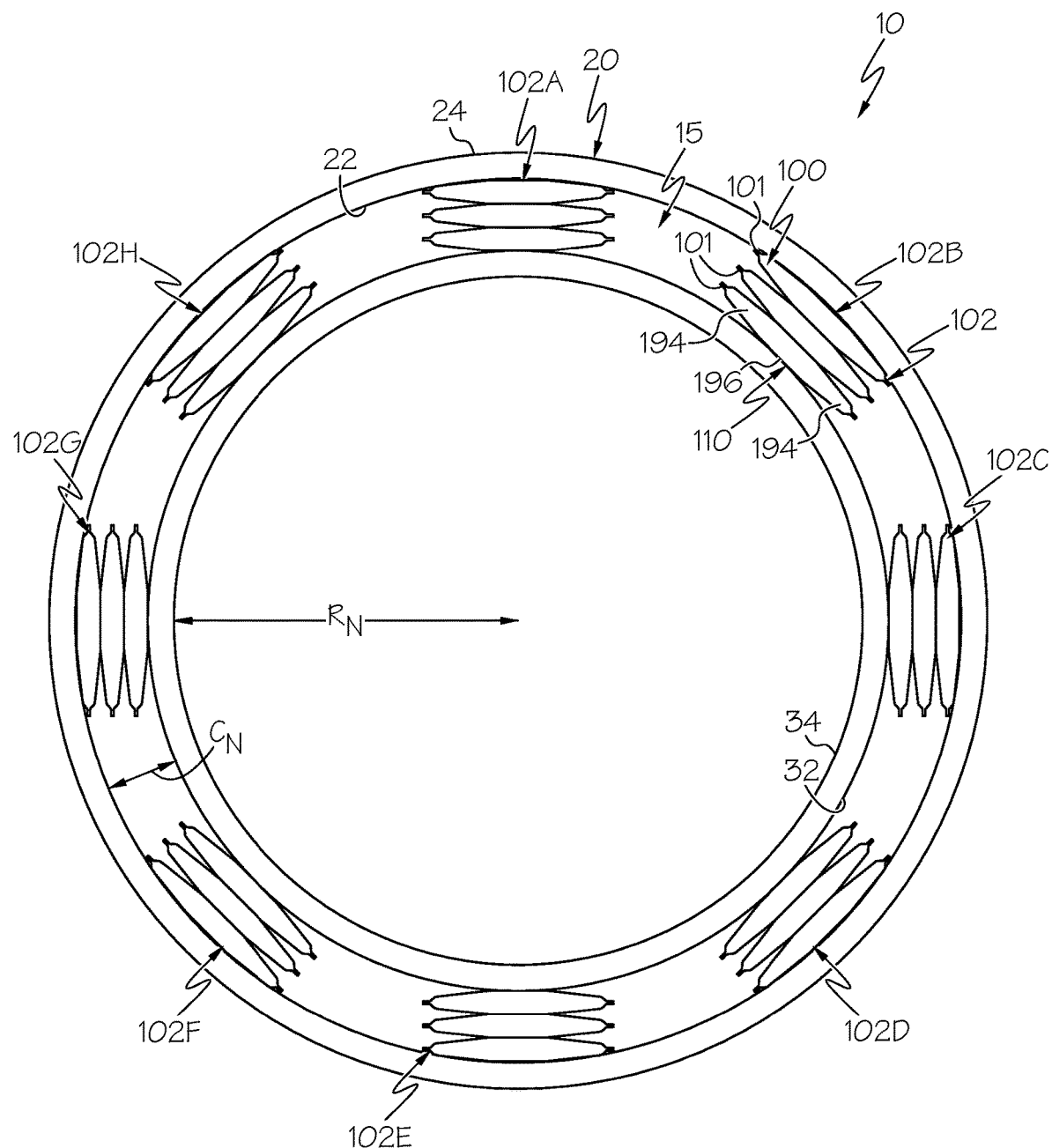
FIG. 2A schematically depicts a cross section of the appendage pressurization device of FIGS. 1A-C showing eight stacks of artificial muscles of the appendage pressurization device in a non-actuated state, according to one or more embodiments shown and described herein.
Figure 2B:
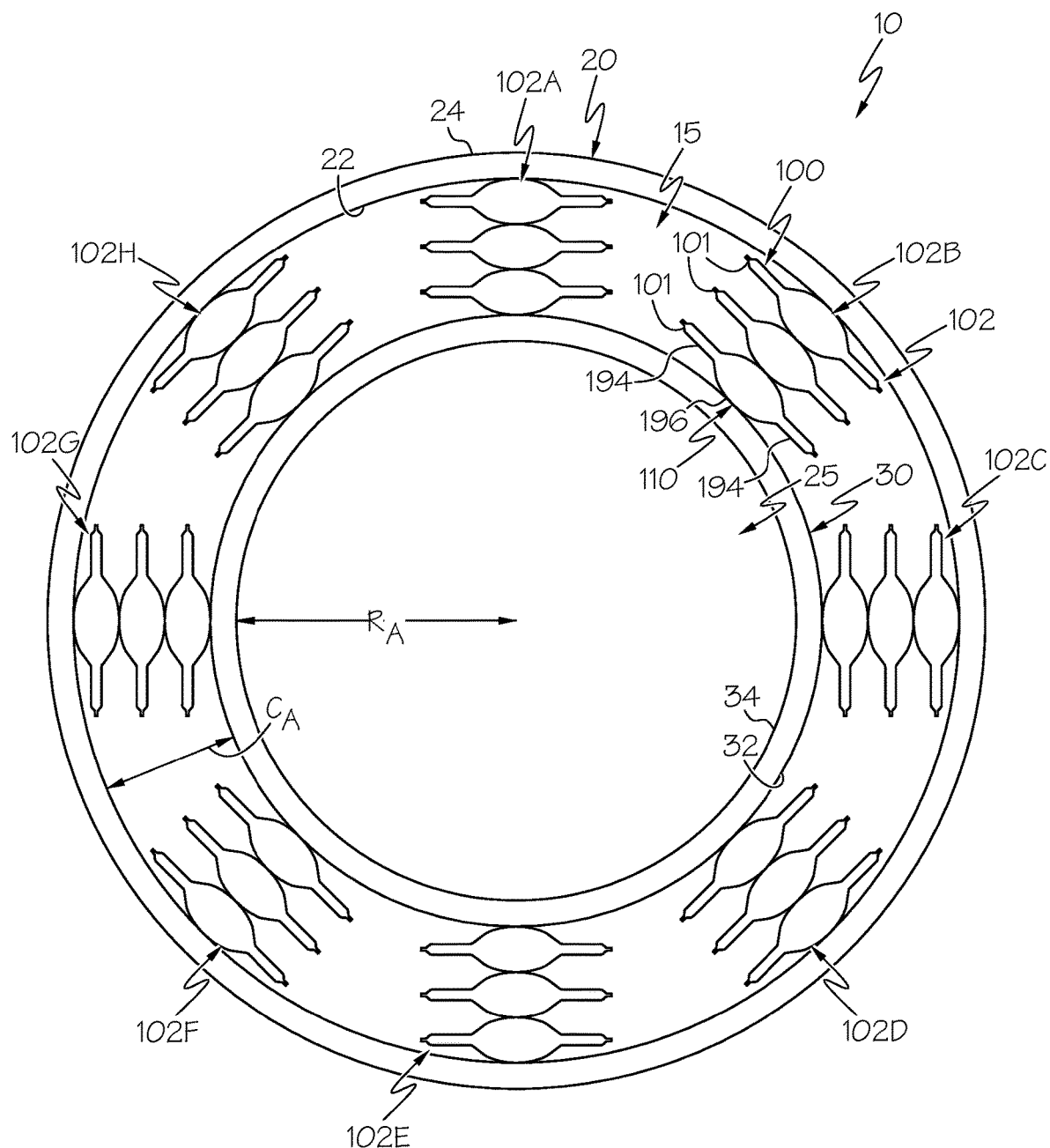
FIG. 2B schematically depicts a cross section of the appendage pressurization device of FIG. 2A showing the eight stacks of artificial muscles of the appendage pressurization device in an actuated state, according to one or more embodiments shown and described herein.
Figure 2C:
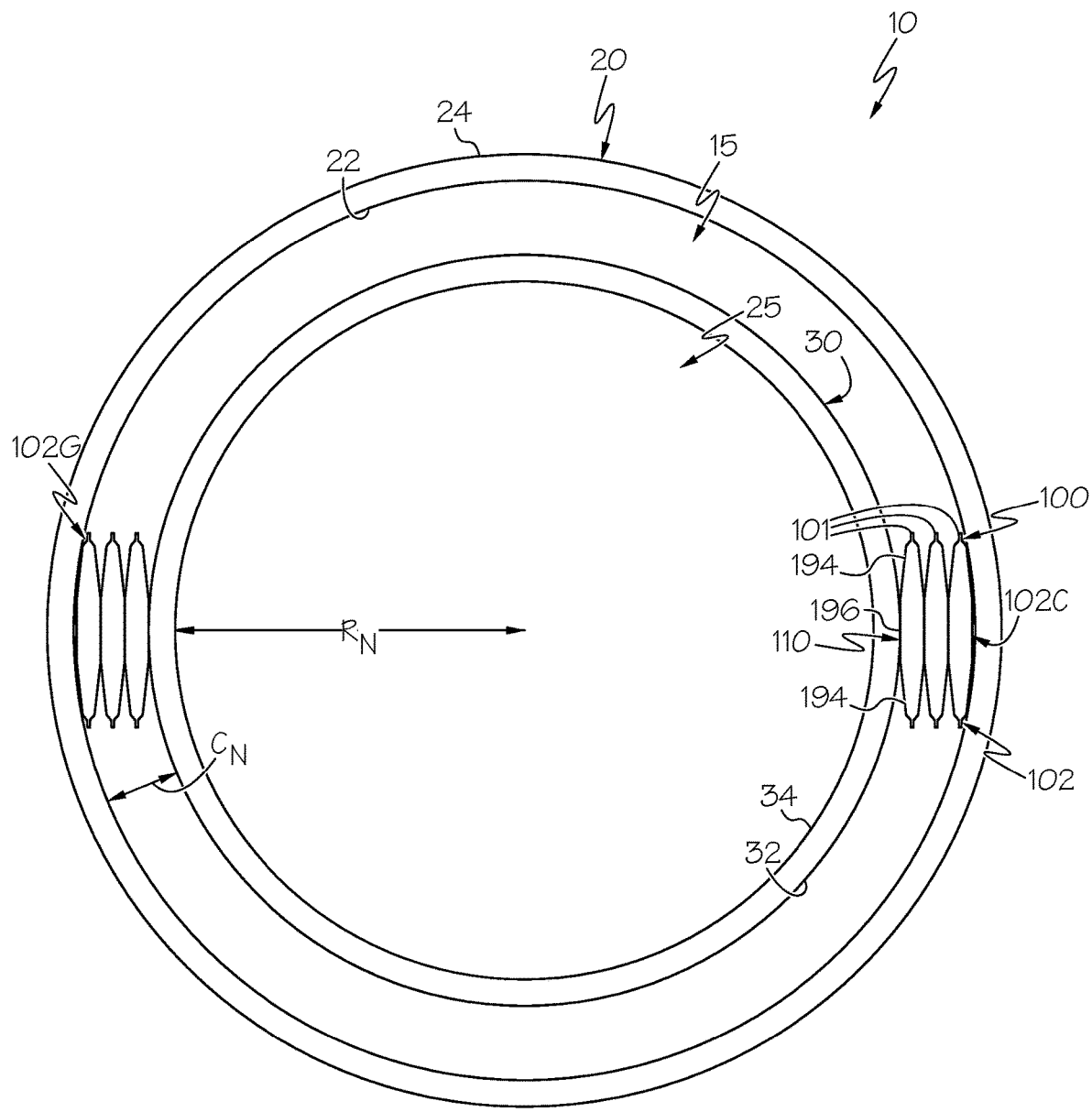
FIG. 2C schematically depicts a cross section of another embodiment of the appendage pressurization device of FIGS. 1A-C showing two stacks of artificial muscles of the appendage pressurization device in the non-actuated state, according to one or more embodiments shown and described herein.
Figure 2D:
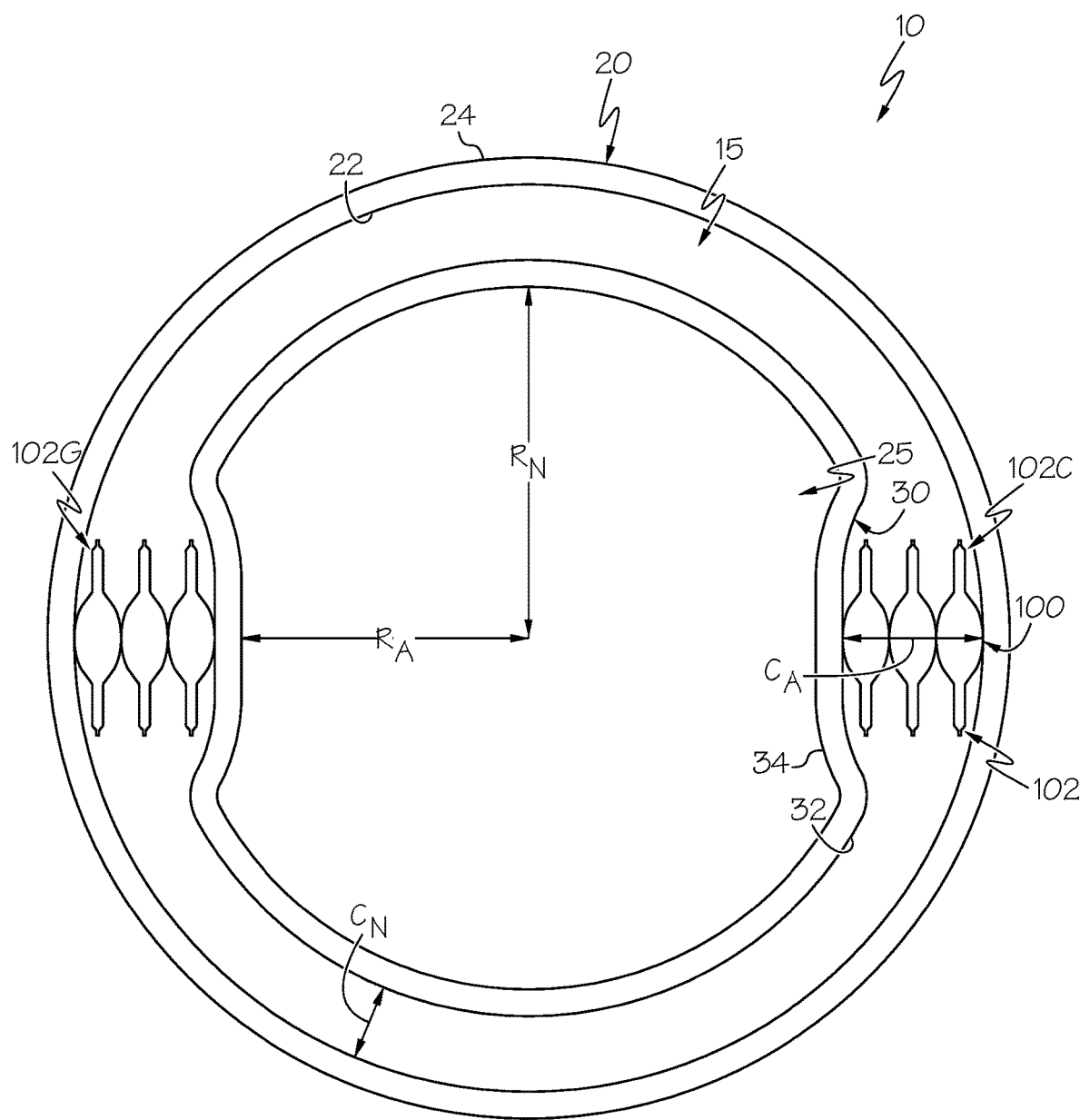
FIG. 2D schematically depicts a cross section of the appendage pressurization device of FIG. 2C showing the two stacks of artificial muscles of the appendage pressurization device in an actuated state, according to one or more embodiments shown and described herein.

Referring again to FIGS. 2A-2D, the plurality of artificial muscles 100 are arranged in a plurality of artificial muscles stacks 102. FIGS. 2A and 2B depict an embodiment having eight artificial muscles stacks 102A-102H in both a non-actuated state (FIG. 2A) and an actuated state (FIG. 2B) and FIGS. 2C and 2D depict an embodiment having two artificial muscle stacks 102C and 102G in both a non-actuated state (FIG. 2C) and an actuated state (FIG. 2D). While these illustrative embodiments comprise two or eight artificial muscles stacks 102A-H, but it should be understood that any number of artificial muscles stacks 102 are contemplated. In some embodiments, the plurality of artificial muscles 101 may be arranged uniformly between the inner layer 30 and the outer layer 20, encircling the inner layer 30 in a uniform radial array at one or multiple lengthwise positions along the length of the appendage strap 12 from the first end 14 to the second end 16. In some embodiments, the expandable fluid region 196 of each artificial muscle 101 of each of the plurality of artificial muscle stacks 102 are coaxially aligned with one another. However, in other embodiments, there may be some offset between the expandable fluid region 196 at least some of the artificial muscles 101 of the plurality of artificial muscles stacks 102. Moreover, while FIG. 2A-2D depict a plurality of artificial muscle stacks 102, embodiments are contemplated in which the plurality of artificial muscles 100 are arranged in a single layer within the cavity 15. This single layer may comprise a radial array of artificial muscles 101 encircling the inner layer 30 (uniformly or non-uniformly) at one or multiple lengthwise positions along the length of the appendage strap 12 from the first end 14 to the second end 16.

The one or more artificial muscles 101 each include an electrode pair 104 disposed in a housing 110 together with a dielectric fluid 198 (FIGS. 4-9). The electrode pair 104 is disposed in an electrode region 194 of the housing 110, adjacent an expandable fluid region 196. In operation, voltage may be applied to the electrode pair 104, drawing the electrode pair 104 together, which directs dielectric fluid into the expandable fluid region 196, expanding the expandable fluid region 196. In FIGS. 2A and 2C, the one or more artificial muscles 101 are each in a non-actuated state. When the plurality of artificial muscles 100 are not actuated, the appendage opening 25 comprises a non-actuated radius $R_N$ and the cavity 15 comprises a non-actuated thickness $C_N$. When the plurality of artificial muscles 100 are actuated, the appendage opening 25 comprises an actuated radius $R_A$ and the cavity 15 comprises an actuated thickness $C_A$. As actuation of the plurality of artificial muscles 100 presses the inner layer 30 inward, the actuated radius $R_A$ is smaller than the non-actuated radius $R_N$ and the actuated thickness $C_A$ of the cavity 15 is larger than the non-actuated thickness $C_N$ of the cavity 15. In operation, when the user 1 is wearing the appendage strap 12, this radial constriction of the inner layer 30 induced by the actuation of the one or more artificial muscles 101 applies pressure to the appendage 2 of the user 1.

While FIGS. 2A and 2C show complete non-actuated states of the cross section of the appendage strap 12, and complete actuated states of the cross section of the appendage strap 12 are depicted in FIGS. 2B and 2D, it should be understood that each individual artificial muscle 101 and each individual artificial muscle stack 102 may be independently actuated to provide selective pressure to the appendage 2 of the user 1. Additionally, the appendage opening 25 in the example depicted in FIG. 2D has multiple radii. In particular, the appendage opening 25 in FIG. 2D has sections with the actuated radius $R_A$ (i.e., sections aligned with the artificial muscle stacks 102C, 102G) and sections with the non-actuated radius $R_N$ (i.e., sections without artificial muscle stacks). It should be understood that multiple radii of the appendage opening 25 may also be achieved by actuation some but not all of artificial muscle stacks 102.

Referring again to FIGS. 2A-2D, in some embodiments, the outer layer 20 of the appendage strap 12 (e.g., an inner diameter of the outer layer 20 of the appendage strap 12) is adjustable to fit onto a variety of different appendage sizes. This adjustability may be achieved by a variety of mechanical features, such as adjustable straps. The appendage pressurization device 10 may be operable to apply selective pressure to the appendage 2 of the user 1 by actuation of the one or more artificial muscles 101. To actuate the appendage pressurization device 10, voltage may be selectively applied to the one or more artificial muscles 101, expanding the expandable fluid regions 196 of the actuated artificial muscles 101.

In some embodiments, each of the one or more artificial muscles 101 are independently actuatable to apply selective pressure to the inner layer 30 of the appendage strap 12, which, when worn, applies selective pressure to the appendage 2. Specifically, appendage straps 12 may be used to hold the connectors 4 and joint 6 of the appendage brace 3 in place, even as the appendage 2 moves and/or its softness, circumference, and/or shape changes over time. For example, the plurality of artificial muscles 100 may be selectively actuated to modify the radius of the appendage opening 25 to the appendage strap 12 to account for appendage muscular changes arising from muscles expanding/contracting and/or having an appendage pressurization device 10 wrapped around the appendage 2. Further to this example, the appendage brace 3 may begin slipping from the appendage 2 or becoming too tight, due to movement and/or temporary changes in the circumference and/or shape of the appendage 2. In this case, the pressure exerted by the appendage straps 12 may be increased or decreased, respectively. This in turn compensates for the slippage or tightness of the appendage brace 3 with respect to the appendage 2. Therefore, the appendage straps 12 are able to compensate to maintain a consistent amount of pressure to maintain a consistent hold of the appendage brace 3 upon the appendage 2.

In embodiments comprising the plurality of artificial muscle stacks 102, each artificial muscle stack 102 may be independently actuatable. Moreover, the artificial muscles 101 of a single artificial muscle stack 102 may also be independently actuatable, allowing the displacement stoke applied by a single artificial muscle stack 102 to be altered based on the number of individual artificial muscles 101 of the single artificial muscle stack 102 that are actuated. This facilitates an amount of pressure applied to the appendage 2. For example, a first artificial muscle stack may be actuated to increase the pressure exerted by an appendage strap 12, while a second artificial muscle stack may not be actuated, or actuated to a lesser extent, based upon the amount of pressure needed at a given time. If further pressure becomes necessary, the second artificial muscle stack can be actuated further.

Figure 3:
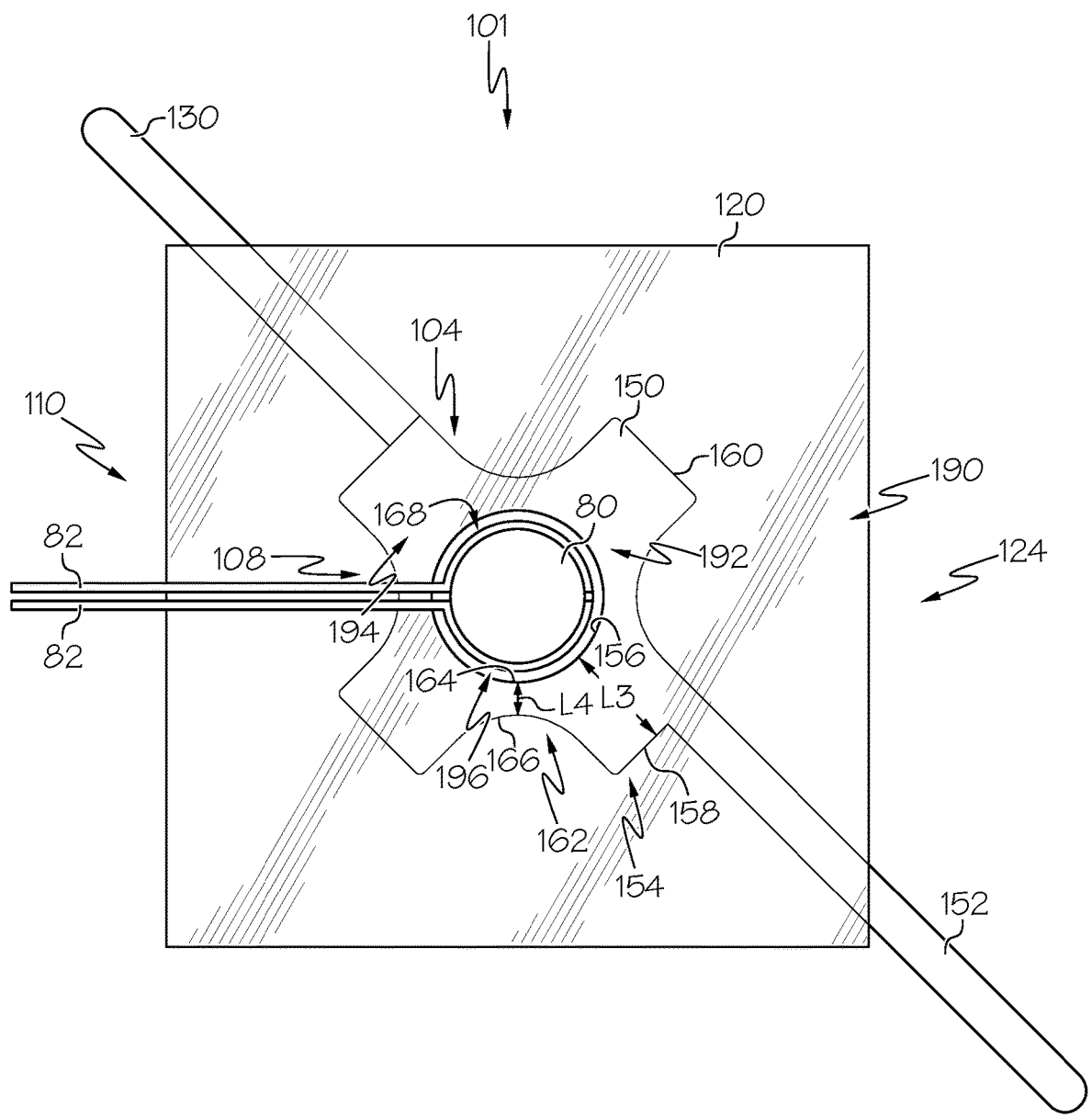
FIG. 3 schematically depicts a top view of an illustrative artificial muscle of the appendage pressurization device of FIGS. 1A-C with a pressure sensor affixed thereon, according to one or more embodiments shown and described herein.
Figure 4:
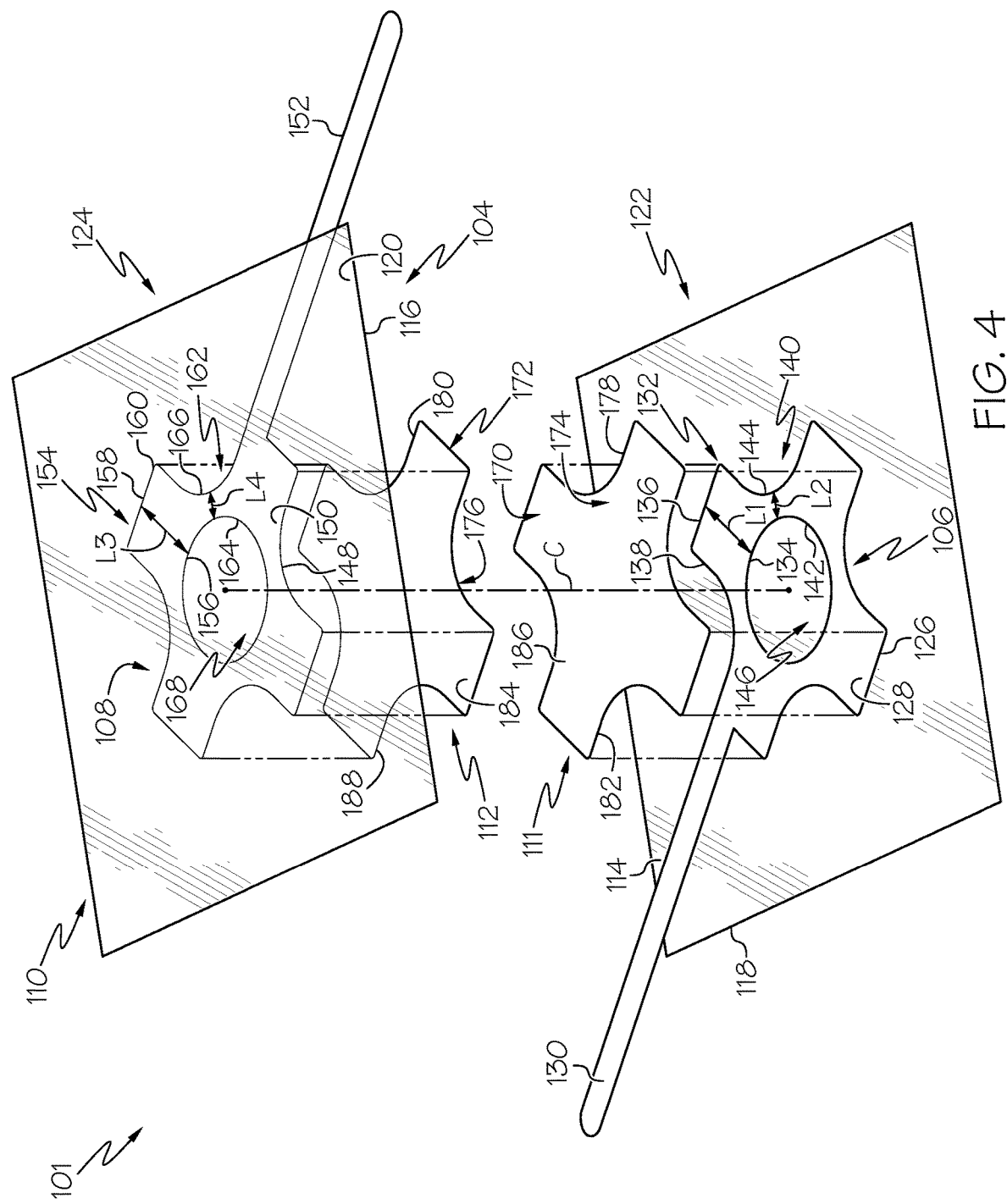
FIG. 4 schematically depicts an exploded view of the artificial muscle of FIG. 3 without the pressure sensor affixed thereon, according to one or more embodiments shown and described herein.
Figure 5:
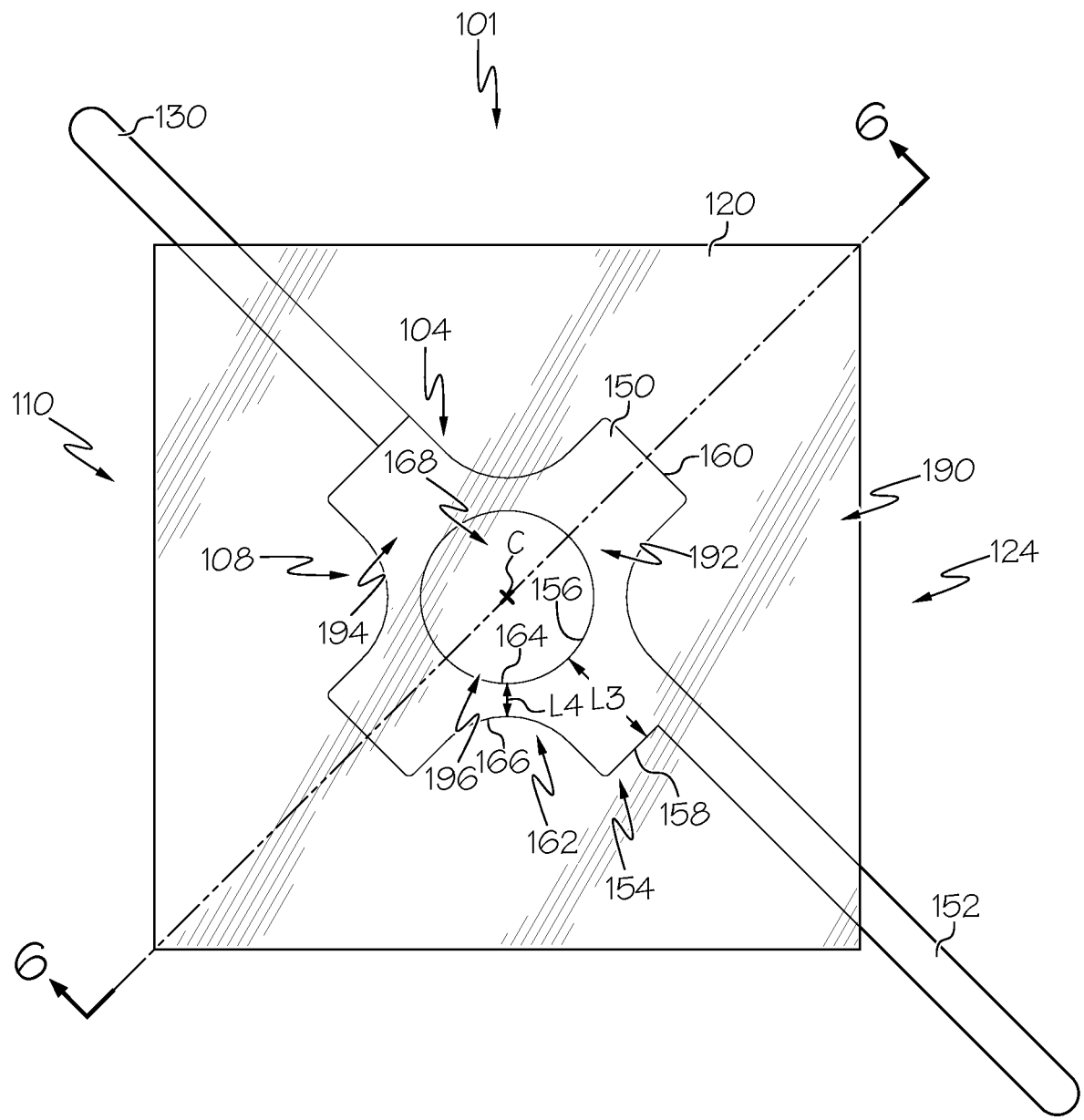
FIG. 5 schematically depicts a top view of the artificial muscle of FIG. 4, according to one or more embodiments shown and described herein.

Referring now to FIGS. 3-5, an example artificial muscle 101 of the appendage pressurization device 10 is depicted in more detail. The artificial muscle 101 includes the housing 110, the electrode pair 104, including a first electrode 106 and a second electrode 108, fixed to opposite surfaces of the housing 110, a first electrical insulator layer 111 fixed to the first electrode 106, and a second electrical insulator layer 112 fixed to the second electrode 108. In some embodiments, the housing 110 is a one-piece monolithic layer including a pair of opposite inner surfaces, such as a first inner surface 114 and a second inner surface 116, and a pair of opposite outer surfaces, such as a first outer surface 118 and a second outer surface 120. In some embodiments, the first inner surface 114 and the second inner surface 116 of the housing 110 are heat-sealable. In other embodiments, the housing 110 may be a pair of individually fabricated film layers, such as a first film layer 122 and a second film layer 124. Thus, the first film layer 122 includes the first inner surface 114 and the first outer surface 118, and the second film layer 124 includes the second inner surface 116 and the second outer surface 120.

While the embodiments described herein primarily refer to the housing 110 as comprising the first film layer 122 and the second film layer 124, as opposed to the one-piece housing, it should be understood that either arrangement is contemplated. In some embodiments, the first film layer 122 and the second film layer 124 generally include the same structure and composition. For example, in some embodiments, the first film layer 122 and the second film layer 124 each comprises biaxially oriented polypropylene.

The first electrode 106 and the second electrode 108 are each positioned between the first film layer 122 and the second film layer 124. In some embodiments, the first electrode 106 and the second electrode 108 are each aluminum-coated polyester such as, for example, Mylar®. In addition, one of the first electrode 106 and the second electrode 108 is a negatively charged electrode and the other of the first electrode 106 and the second electrode 108 is a positively charged electrode. For purposes discussed herein, either electrode 106, 108 may be positively charged so long as the other electrode 106, 108 of the artificial muscle 101 is negatively charged.

Figure 10:
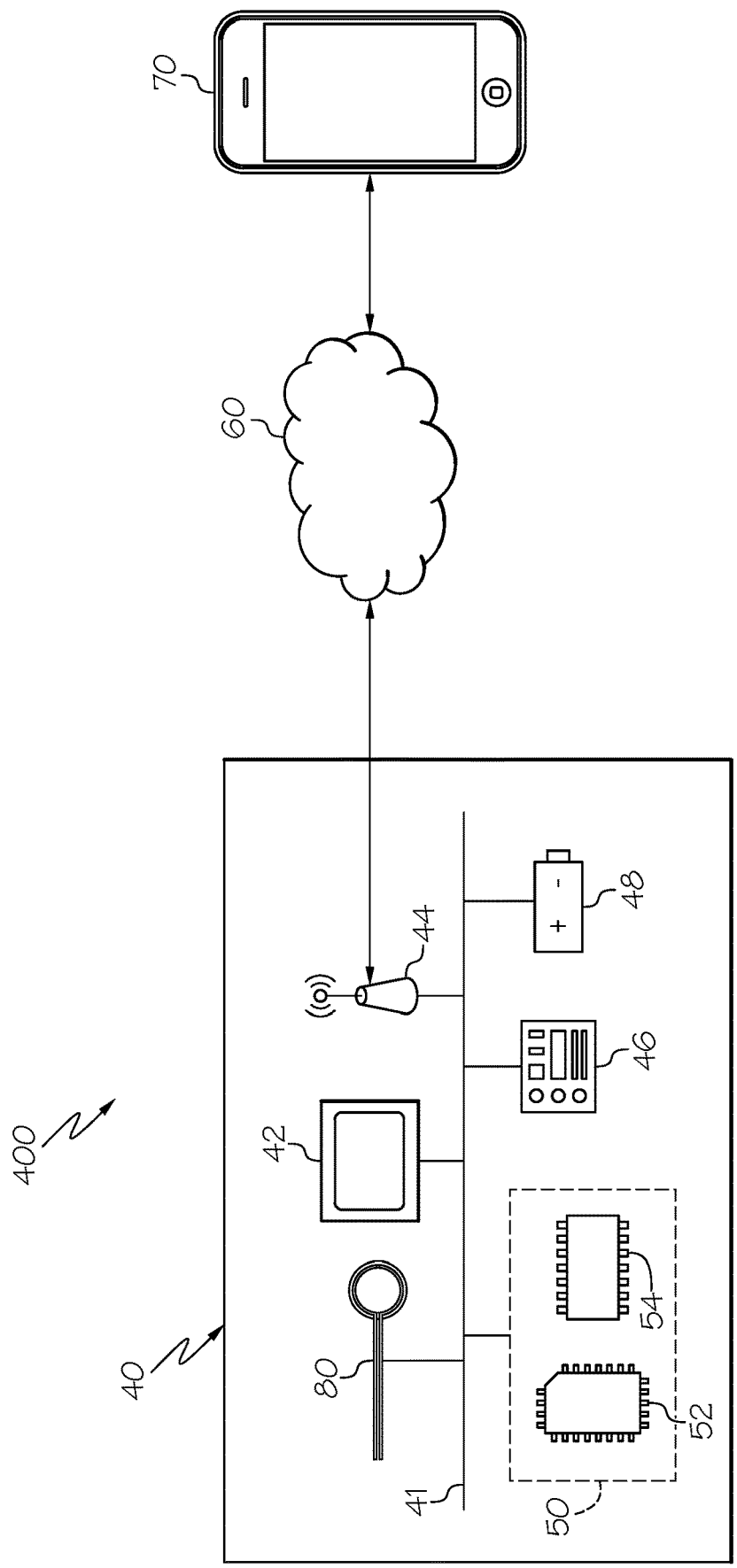
FIG. 10 schematically depicts an actuation system for operating the appendage pressurization device of FIGS. 1A-C, according to one or more embodiments shown and described herein.

The first electrode 106 has a film-facing surface 126 and an opposite inner surface 128. The first electrode 106 is positioned against the first film layer 122, specifically, the first inner surface 114 of the first film layer 122. In addition, the first electrode 106 includes a first terminal 130 extending from the first electrode 106 past an edge of the first film layer 122 such that the first terminal 130 can be connected to a power supply to actuate the first electrode 106. Specifically, the terminal is coupled, either directly or in series, to a power supply and a controller of an actuation system 400, as shown in FIG. 10. Similarly, the second electrode 108 has a film-facing surface 148 and an opposite inner surface 150. The second electrode 108 is positioned against the second film layer 124, specifically, the second inner surface 116 of the second film layer 124. The second electrode 108 includes a second terminal 152 extending from the second electrode 108 past an edge of the second film layer 124 such that the second terminal 152 can be connected to a power supply and a controller of the actuation system 400 to actuate the second electrode 108.

The first electrode 106 includes two or more tab portions 132 and two or more bridge portions 140. Each bridge portion 140 is positioned between adjacent tab portions 132, interconnecting these adjacent tab portions 132. Each tab portion 132 has a first end 134 extending radially from a center axis C of the first electrode 106 to an opposite second end 136 of the tab portion 132, where the second end 136 defines a portion of an outer perimeter 138 of the first electrode 106. Each bridge portion 140 has a first end 142 extending radially from the center axis C of the first electrode 106 to an opposite second end 144 of the bridge portion 140 defining another portion of the outer perimeter 138 of the first electrode 106. Each tab portion 132 has a tab length L1 and each bridge portion 140 has a bridge length L2 extending in a radial direction from the center axis C of the first electrode 106. The tab length L1 is a distance from the first end 134 to the second end 136 of the tab portion 132 and the bridge length L2 is a distance from the first end 142 to the second end 144 of the bridge portion 140. The tab length L1 of each tab portion 132 is longer than the bridge length L2 of each bridge portion 140. In some embodiments, the bridge length L2 is 20% to 50% of the tab length L1, such as 30% to 40% of the tab length L1.

In some embodiments, the two or more tab portions 132 are arranged in one or more pairs of tab portions 132. Each pair of tab portions 132 includes two tab portions 132 arranged diametrically opposed to one another. In some embodiments, the first electrode 106 may include only two tab portions 132 positioned on opposite sides or ends of the first electrode 106. In some embodiments, as shown in FIGS. 3-5, the first electrode 106 includes four tab portions 132 and four bridge portions 140 interconnecting adjacent tab portions 132. In this embodiment, the four tab portion 132 are arranged as two pairs of tab portions 132 diametrically opposed to one another. Furthermore, as shown, the first terminal 130 extends from the second end 136 of one of the tab portions 132 and is integrally formed therewith.

Like the first electrode 106, the second electrode 108 includes at least a pair of tab portions 154 and two or more bridge portions 162. Each bridge portion 162 is positioned between adjacent tab portions 154, interconnecting these adjacent tab portions 154. Each tab portion 154 has a first end 156 extending radially from a center axis C of the second electrode 108 to an opposite second end 158 of the tab portion 154, where the second end 158 defines a portion of an outer perimeter 160 of the second electrode 108. Due to the first electrode 106 and the second electrode 108 being coaxial with one another, the center axis C of the first electrode 106 and the second electrode 108 are the same. Each bridge portion 162 has a first end 164 extending radially from the center axis C of the second electrode to an opposite second end 166 of the bridge portion 162 defining another portion of the outer perimeter 160 of the second electrode 108. Each tab portion 154 has a tab length L3 and each bridge portion 162 has a bridge length L4 extending in a radial direction from the center axis C of the second electrode 108. The tab length L3 is a distance from the first end 156 to the second end 158 of the tab portion 154 and the bridge length L4 is a distance from the first end 164 to the second end 166 of the bridge portion 162. The tab length L3 is longer than the bridge length L4 of each bridge portion 162. In some embodiments, the bridge length L4 is 20% to 50% of the tab length L3, such as 30% to 40% of the tab length L3.

In some embodiments, the two or more tab portions 154 are arranged in one or more pairs of tab portions 154. Each pair of tab portions 154 includes two tab portions 154 arranged diametrically opposed to one another. In some embodiments, the second electrode 108 may include only two tab portions 154 positioned on opposite sides or ends of the first electrode 106. In some embodiments, as shown in FIGS. 3-5, the second electrode 108 includes four tab portions 154 and four bridge portions 162 interconnecting adjacent tab portions 154. In this embodiment, the four tab portions 154 are arranged as two pairs of tab portions 154 diametrically opposed to one another. Furthermore, as shown, the second terminal 152 extends from the second end 158 of one of the tab portions 154 and is integrally formed therewith.

Figure 6:
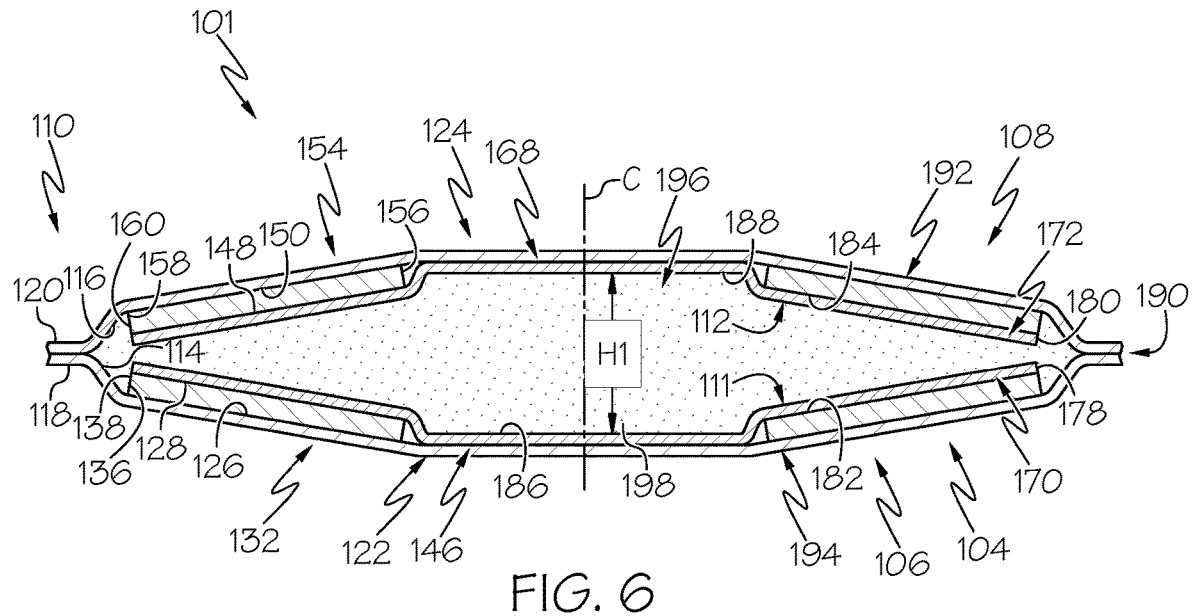
FIG. 6 schematically depicts a cross-sectional view of the artificial muscle of FIG. 4 taken along line 6-6 in FIG. 4 in a non-actuated state, according to one or more embodiments shown and described herein.
Figure 7:
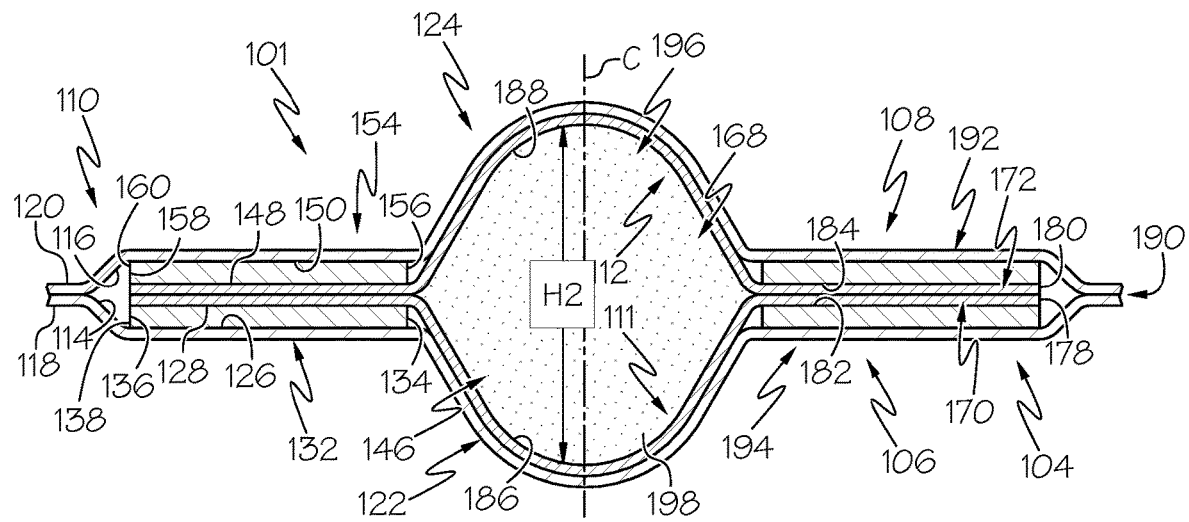
FIG. 7 schematically depicts a cross-sectional view of the artificial muscle of FIG. 4 taken along line 6-6 in FIG. 4 in an actuated state, according to one or more embodiments shown and described herein.
Figure 8:
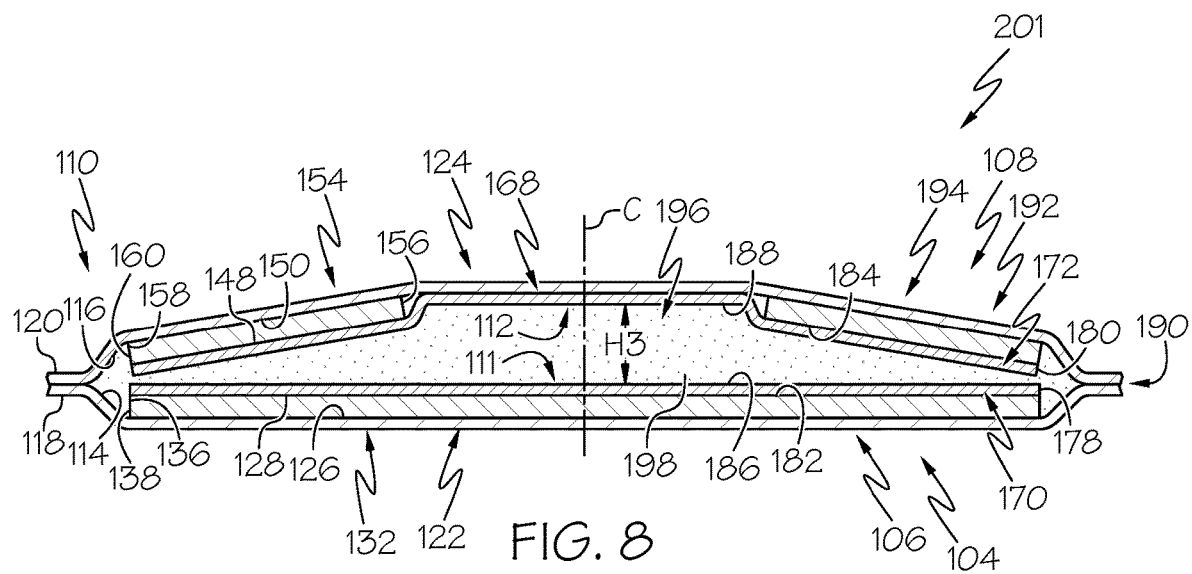
FIG. 8 schematically depicts a cross-sectional view of another illustrative artificial muscle in a non-actuated state, according to one or more embodiments shown and described herein.
Figure 9:
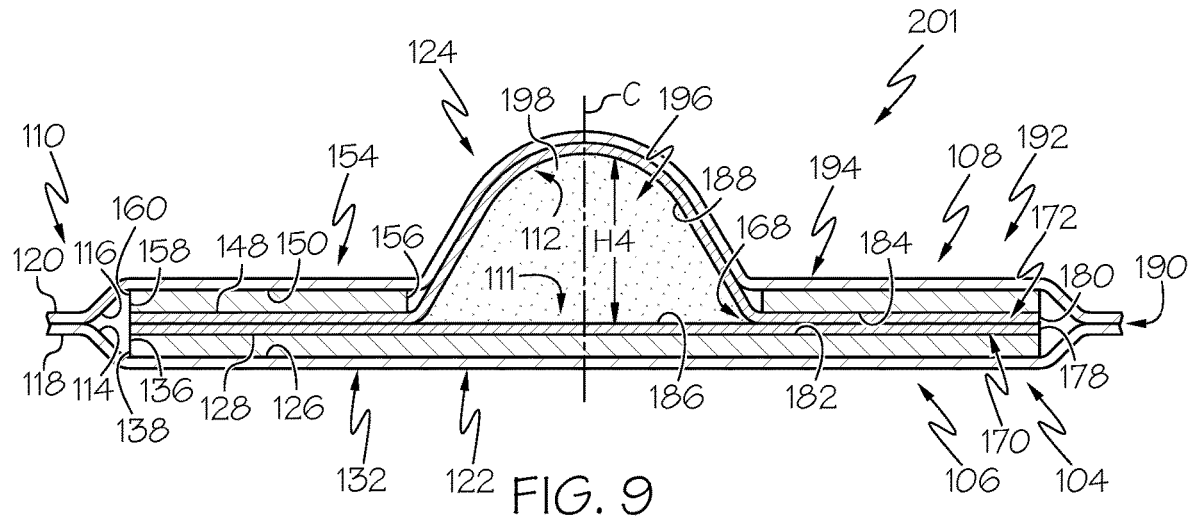
FIG. 9 schematically depicts a cross-sectional view of the artificial muscle of FIG. 8 in an actuated state, according to one or more embodiments shown and described herein.

Referring now to FIGS. 3-9, at least one of the first electrode 106 and the second electrode 108 has a central opening formed therein between the first end 134 of the tab portions 132 and the first end 142 of the bridge portions 140. In FIGS. 6 and 7, the first electrode 106 has a central opening 146. However, it should be understood that the first electrode 106 does not need to include the central opening 146 when a central opening is provided within the second electrode 108, as shown in FIGS. 8 and 9. Alternatively, the second electrode 108 does not need to include the central opening when the central opening 146 is provided within the first electrode 106. Referring to FIGS. 3-9, the first electrical insulator layer 111 and the second electrical insulator layer 112 have a geometry generally corresponding to the first electrode 106 and the second electrode 108, respectively. Thus, the first electrical insulator layer 111 and the second electrical insulator layer 112 each have tab portions 170, 172 and bridge portions 174, 176 corresponding to like portions on the first electrode 106 and the second electrode 108. Further, the first electrical insulator layer 111 and the second electrical insulator layer 112 each have an outer perimeter 178, 180 corresponding to the outer perimeter 138 of the first electrode 106 and the outer perimeter 160 of the second electrode 108, respectively, when positioned thereon.

It should be appreciated that, in some embodiments, the first electrical insulator layer 111 and the second electrical insulator layer 112 generally include the same structure and composition. As such, in some embodiments, the first electrical insulator layer 111 and the second electrical insulator layer 112 each include an adhesive surface 182, 184 and an opposite non-sealable surface 186, 188, respectively. Thus, in some embodiments, the first electrical insulator layer 111 and the second electrical insulator layer 112 are each a polymer tape adhered to the inner surface 128 of the first electrode 106 and the inner surface 150 of the second electrode 108, respectively.

Referring again to FIGS. 3-9, the artificial muscle 101 is shown in its assembled form with the first terminal 130 of the first electrode 106 and the second terminal 152 of the second electrode 108 extending past an outer perimeter of the housing 110, i.e., the first film layer 122 and the second film layer 124. As shown in FIG. 4, the second electrode 108 is stacked on top of the first electrode 106 and, therefore, the first electrode 106, the first film layer 122, and the second film layer 124 are not shown. In its assembled form, the first electrode 106, the second electrode 108, the first electrical insulator layer 111, and the second electrical insulator layer 112 are sandwiched between the first film layer 122 and the second film layer 124. The first film layer 122 is partially sealed to the second film layer 124 at an area surrounding the outer perimeter 138 of the first electrode 106 and the outer perimeter 160 of the second electrode 108. In some embodiments, the first film layer 122 is heat-sealed to the second film layer 124. Specifically, in some embodiments, the first film layer 122 is sealed to the second film layer 124 to define a sealed portion 190 surrounding the first electrode 106 and the second electrode 108. The first film layer 122 and the second film layer 124 may be sealed in any suitable manner, such as using an adhesive, heat sealing, or the like.

The first electrode 106, the second electrode 108, the first electrical insulator layer 111, and the second electrical insulator layer 112 provide a barrier that prevents the first film layer 122 from sealing to the second film layer 124 forming an unsealed portion 192. The unsealed portion 192 of the housing 110 includes the electrode region 194, in which the electrode pair 104 is provided, and the expandable fluid region 196, which is surrounded by the electrode region 194. The central openings 146, 168 of the first electrode 106 and the second electrode 108 form the expandable fluid region 196 and are arranged to be axially stacked on one another. Although not shown, the housing 110 may be cut to conform to the geometry of the electrode pair 104 and reduce the size of the artificial muscle 101, namely, the size of the sealed portion 190.

A dielectric fluid 198 is provided within the unsealed portion 192 and flows freely between the first electrode 106 and the second electrode 108. A "dielectric" fluid as used herein is a medium or material that transmits electrical force without conduction and as such has low electrical conductivity. Some non-limiting example dielectric fluids include perfluoroalkanes, transformer oils, and deionized water. It should be appreciated that the dielectric fluid 198 may be injected into the unsealed portion 192 of the artificial muscle 101 using a needle or other suitable injection device.

Referring now to FIGS. 6 and 7, the artificial muscle 101 is actuatable between a non-actuated state and an actuated state. In the non-actuated state, as shown in FIG. 6, the first electrode 106 and the second electrode 108 are partially spaced apart from one another proximate the central openings 146, 168 thereof and the first end 134, 156 of the tab portions 132, 154. The second end 136, 158 of the tab portions 132, 154 remain in position relative to one another due to the housing 110 being sealed at the outer perimeter 138 of the first electrode 106 and the outer perimeter 160 of the second electrode 108. In FIGS. 2A and 2C, at least one of the one or more artificial muscles 101 of the appendage pressurization device 10 is in the non-actuated state. In the actuated state, as shown in FIG. 7, the first electrode 106 and the second electrode 108 are brought into contact with and oriented parallel to one another to force the dielectric fluid 198 into the expandable fluid region 196. This causes the dielectric fluid 198 to flow through the central openings 146, 168 of the first electrode 106 and the second electrode 108 and inflate the expandable fluid region 196. In FIGS. 2B and 2D, at least one of the one or more artificial muscles 101 of the appendage pressurization device 10 is in the actuated state.

Referring now to FIG. 6, the artificial muscle 101 is shown in the non-actuated state. The electrode pair 104 is provided within the electrode region 194 of the unsealed portion 192 of the housing 110. The central opening 146 of the first electrode 106 and the central opening 168 of the second electrode 108 are coaxially aligned within the expandable fluid region 196. In the non-actuated state, the first electrode 106 and the second electrode 108 are partially spaced apart from and non-parallel to one another. Due to the first film layer 122 being sealed to the second film layer 124 around the electrode pair 104, the second end 136, 158 of the tab portions 132, 154 are brought into contact with one another. Thus, dielectric fluid 198 is provided between the first electrode 106 and the second electrode 108, thereby separating the first end 134, 156 of the tab portions 132, 154 proximate the expandable fluid region 196. Stated another way, a distance between the first end 134 of the tab portion 132 of the first electrode 106 and the first end 156 of the tab portion 154 of the second electrode 108 is greater than a distance between the second end 136 of the tab portion 132 of the first electrode 106 and the second end 158 of the tab portion 154 of the second electrode 108. This results in the electrode pair 104 zippering toward the expandable fluid region 196 when actuated. In some embodiments, the first electrode 106 and the second electrode 108 may be flexible. Thus, as shown in FIG. 4, the first electrode 106 and the second electrode 108 are convex such that the second ends 136, 158 of the tab portions 132, 154 thereof may remain close to one another, but spaced apart from one another proximate the central openings 146, 168. In the non-actuated state, the expandable fluid region 196 has a first height H1.

When actuated, as shown in FIG. 7, the first electrode 106 and the second electrode 108 zipper toward one another from the second ends 144, 158 of the tab portions 132, 154 thereof, thereby pushing the dielectric fluid 198 into the expandable fluid region 196. As shown, when in the actuated state, the first electrode 106 and the second electrode 108 are parallel to one another. In the actuated state, the dielectric fluid 198 flows into the expandable fluid region 196 to inflate the expandable fluid region 196. As such, the first film layer 122 and the second film layer 124 expand in opposite directions. In the actuated state, the expandable fluid region 196 has a second height H2, which is greater than the first height H1 of the expandable fluid region 196 when in the non-actuated state. Although not shown, it should be noted that the electrode pair 104 may be partially actuated to a position between the non-actuated state and the actuated state. This would allow for partial inflation of the expandable fluid region 196 and adjustments when necessary.

In order to move the first electrode 106 and the second electrode 108 toward one another, a voltage is applied by a power supply (such as power supply 48 of FIG. 10). In some embodiments, a voltage of up to 10 kV may be provided from the power supply to induce an electric field through the dielectric fluid 198. The resulting attraction between the first electrode 106 and the second electrode 108 pushes the dielectric fluid 198 into the expandable fluid region 196. Pressure from the dielectric fluid 198 within the expandable fluid region 196 causes the first film layer 122 and the first electrical insulator layer 111 to deform in a first axial direction along the center axis C of the first electrode 106 and causes the second film layer 124 and the second electrical insulator layer 112 to deform in an opposite second axial direction along the center axis C of the second electrode 108. Once the voltage being supplied to the first electrode 106 and the second electrode 108 is discontinued, the first electrode 106 and the second electrode 108 return to their initial, non-parallel position in the non-actuated state.

It should be appreciated that the present embodiments of the artificial muscle 101 disclosed herein, specifically, the tab portions 132, 154 with the interconnecting bridge portions 174, 176, provide a number of improvements over actuators that do not include the tab portions 132, 154, such as hydraulically amplified self-healing electrostatic (HA-SEL) actuators described in the paper titled "*Hydraulically amplified self-healing electrostatic actuators with muscle-like performance*" by E. Acome, S. K. Mitchell, T. G. Morrissey, M. B. Emmett, C. Benjamin, M. King, M. Radakovitz, and C. Keplinger (Science 5 Jan. 2018: Vol. 359, Issue 6371, pp. 61-65). Embodiments of the artificial muscle 101 including two pairs of tab portions 132, 154 on each of the first electrode 106 and the second electrode 108, respectively, reduces the overall mass and thickness of the artificial muscle 101, reduces the amount of voltage required during actuation, and decreases the total volume of the artificial muscle 101 without reducing the amount of resulting force after actuation as compared to known HASEL actuators including donut-shaped electrodes having a uniform, radially-extending width. More particularly, the tab portions 132, 154 of the artificial muscle 101 provide zipping fronts that result in increased actuation power by providing localized and uniform hydraulic actuation of the artificial muscle 101 compared to HASEL actuators including donut-shaped electrodes. Specifically, one pair of tab portions 132, 154 provides twice the amount of actuator power per unit volume as compared to donut-shaped HASEL actuators, while two pairs of tab portions 132, 154 provide four times the amount of actuator power per unit volume. The bridge portions 174, 176 interconnecting the tab portions 132, 154 also limit buckling of the tab portions 132, 154 by maintaining the distance between adjacent tab portions 132, 154 during actuation. Because the bridge portions 174, 176 are integrally formed with the tab portions 132, 154, the bridge portions 174, 176 also prevent leakage between the tab portions 132, 154 by eliminating attachment locations that provide an increased risk of rupturing.

In operation, when the artificial muscle 101 is actuated, expansion of the expandable fluid region 196 produces a force of 3 Newton-millimeters (N·mm) per cubic centimeter (cm³) of actuator volume or greater, such as 4 N·mm per cm³ or greater, 5 N·mm per cm³ or greater, 6 N·mm per cm³ or greater, 7 N·mm per cm³ or greater, 8 N·mm per cm³ or greater, or the like. In one example, when the artificial muscle 101 is actuated by a voltage of 9.5 kilovolts (kV), the artificial muscle 101 provides a resulting force of 5 N. In another example, when the artificial muscle 101 is actuated by a voltage of 10 kV the artificial muscle 101 provides 440% strain under a 500 gram load.

Moreover, the size of the first electrode 106 and the second electrode 108 is proportional to the amount of displacement of the dielectric fluid 198. Therefore, when greater displacement within the expandable fluid region 196 is desired, the size of the electrode pair 104 is increased relative to the size of the expandable fluid region 196. It should be appreciated that the size of the expandable fluid region 196 is defined by the central openings 146, 168 in the first electrode 106 and the second electrode 108. Thus, the degree of displacement within the expandable fluid region 196 may alternatively, or in addition, be controlled by increasing or reducing the size of the central openings 146, 168.

As shown in FIGS. 8 and 9, another embodiment of an artificial muscle 201 is illustrated. The artificial muscle 201 is substantially similar to the artificial muscle 101. As such, like structure is indicated with like reference numerals. However, as shown, the first electrode 106 does not include a central opening. Thus, only the second electrode 108 includes the central opening 168 formed therein. As shown in FIG. 8, the artificial muscle 201 is in the non-actuated state with the first electrode 106 being planar and the second electrode 108 being convex relative to the first electrode 106. In the non-actuated state, the expandable fluid region 196 has a first height H3. In the actuated state, as shown in FIG. 9, the expandable fluid region 196 has a second height H4, which is greater than the first height H3. It should be appreciated that by providing the central opening 168 only in the second electrode 108 as opposed to both the first electrode 106 and the second electrode 108, the total deformation may be formed on one side of the artificial muscle 201. In addition, because the total deformation is formed on only one side of the artificial muscle 201, the second height H4 of the expandable fluid region 196 of the artificial muscle 201 extends further from a longitudinal axis perpendicular to the central axis C of the artificial muscle 201 than the second height H2 of the expandable fluid region 196 of the artificial muscle 101 when all other dimensions, orientations, and volume of dielectric fluid are the same. It should be understood that embodiments of the artificial muscle 201 may be used together with or in place of the one or more artificial muscles 101 of the appendage pressurization device 10 of FIGS. 1A-2D.

In some embodiments, as shown in FIG. 3, a pressure sensor 80 may reside on the housing 110 and be aligned with the central opening 168 or central opening 146, which are openings in the first electrode 106 and second electrode 108, respectively. In some embodiments, the pressure sensor 80 may be disposed on the expandable fluid region 196 of the housing 110. In other embodiments, the pressure sensor 80 may be located on any suitable surface of the housing 110 or an artificial muscle 101. The pressure sensor 80 is utilized to measure pressure exerted in the appendage strap 12 to maintain a proper fit of the appendage brace 3 on an appendage 2 of the user 1. For example, as a user 1 bends their knee, less pressure will need to be applied by the appendage strap 12 to the appendage 2 because the leg will flex and expand.

In some embodiments, different pressure sensors 80 within the appendage pressurization device 10 may be located at different locations with respect to different housings 110 and/or an artificial muscles 101. In this embodiment, the pressure sensor 80 has two sensor protrusions 82 that extend outwardly from the pressure sensor 80 and may be disposed between the inner layer 30 and outer layer 20. Sensor protrusions may be used, for example, to wirelessly communicate with other components, such as a controller 50 (as shown in FIG. 10) and/or other wireless sensors 80 located on other artificial muscles 101. In other embodiments, any number of sensor protrusions 82 of any shape, size, and/or configuration may be utilized. In still other embodiments, the pressure sensor 80 may have no sensor protrusions 82.

In some embodiments, the pressure sensor 80 may be of any suitable type, such as, by way of non-limiting example, absolute, gauge, or differential pressure sensors. Sensing by the pressure sensor 80 may include any suitable technique such as resistive sensing, capacitive sensing, piezoelectric sensing, optical sensing, micro electro-mechanical system (MEMS), or any other suitable type of pressure sensing technique. Output from the pressure sensor 80 may be by millivolt-output transducers, volt-output transducers, transmitters, or any other suitable components.

Referring now to FIG. 10, an actuation system 400 may be provided for operating the appendage pressurization device 10, in particular, operate the or more artificial muscles 101 of the appendage pressurization device 10. The actuation system 400 may comprise a controller 50, the one or more pressure sensors 80, an operating device 46, a power supply 48, a display device 42, network interface hardware 44, and a communication path 41 communicatively coupled these components, some or all of which may be disposed in the onboard control unit 40.

The controller 50 may comprise a processor 52 and a non-transitory electronic memory 54 to which various components are communicatively coupled. In some embodiments, the processor 52 and the non-transitory electronic memory 54 and/or the other components are included within a single device. In other embodiments, the processor 52 and the non-transitory electronic memory 54 and/or the other components may be distributed among multiple devices that are communicatively coupled. The controller 50 may include non-transitory electronic memory 54 that stores a set of machine-readable instructions. The processor 52 may execute the machine-readable instructions stored in the non-transitory electronic memory 54. The non-transitory electronic memory 54 may comprise RAM, ROM, flash memories, hard drives, or any device capable of storing machine-readable instructions such that the machine-readable instructions can be accessed by the processor 52. Accordingly, the actuation system 400 described herein may be implemented in any computer programming language, as pre-programmed hardware elements, or as a combination of hardware and software components. The non-transitory electronic memory 54 may be implemented as one memory module or a plurality of memory modules. The controller 50 may receive a current pressure value from the pressure sensor 80, output an updated pressure value the pressure sensor 80, and/or modify actuation of at least one of the one or more artificial muscles based upon the updated pressure value to maintain the consistent amount of pressure at the inner layer of the appendage strap. The artificial muscle may be one of a plurality of artificial muscles such that adjusting the actuation of each of the plurality of muscles maintains the consistent amount of pressure at inner layer of the appendage strap. The appendage strap may be coupled to an appendage brace in some embodiments. As discussed further with respect to FIG. 11, the consistent amount of pressure at an inner layer of the inner layer 30 may be maintained based upon a feedback loop maintained by the controller 50 in coordination with one or more pressure sensors 80.

In some embodiments, the non-transitory electronic memory 54 includes instructions for executing the functions of the actuation system 400. The instructions may include instructions for operating the appendage pressurization device 10, for example, instructions for actuating the one or more artificial muscles 101, individually or collectively, and actuating the artificial muscles stacks, individually or collectively.

The processor 52 may be any device capable of executing machine-readable instructions. For example, the processor 52 may be an integrated circuit, a microchip, a computer, or any other computing device. The non-transitory electronic memory 54 and the processor 52 are coupled to the communication path 41 that provides signal interconnectivity between various components and/or modules of the actuation system 400. Accordingly, the communication path 41 may communicatively couple any number of processors with one another, and allow the modules coupled to the communication path 41 to operate in a distributed computing environment. Specifically, each of the modules may operate as a node that may send and/or receive data. As used herein, the term "communicatively coupled" means that coupled components are capable of exchanging data signals with one another such as, for example, electrical signals via conductive medium, electromagnetic signals via air, optical signals via optical waveguides, and the like.

As schematically depicted in FIG. 10, the communication path 41 communicatively couples the processor 52 and the non-transitory electronic memory 54 of the controller 50 with a plurality of other components of the actuation system 400. For example, the actuation system 400 depicted in FIG. 10 includes the processor 52 and the non-transitory electronic memory 54 communicatively coupled with the pressure sensor 80, operating device 46, and the power supply 48.

The operating device 46 allows for a user to control operation of the artificial muscles 101 of the appendage pressurization device 10. In some embodiments, the operating device 46 may be a switch, toggle, button, or any combination of controls to provide user operation. The operating device 46 is coupled to the communication path 41 such that the communication path 41 communicatively couples the operating device 46 to other modules of the actuation system 400. The operating device 46 may provide a user interface for receiving user instructions as to a specific operating configuration of the appendage pressurization device 10, such as maintaining a desired pressure value between the appendage strap 12 and the appendage 2 of the user 1.

The power supply 48 (e.g., battery) provides power to the one or more artificial muscles 101 of the appendage pressurization device 10. In some embodiments, the power supply 48 is a rechargeable direct current power source. It is to be understood that the power supply 48 may be a single power supply or battery for providing power to the one or more artificial muscles 101 of the appendage pressurization device 10. A power adapter (not shown) may be provided and electrically coupled via a wiring harness or the like for providing power to the one or more artificial muscles 101 of the appendage pressurization device 10 via the power supply 48.

In some embodiments, the actuation system 400 also includes a display device 42. The display device 42 is coupled to the communication path 41 such that the communication path 41 communicatively couples the display device 42 to other modules of the actuation system 400. The display device 42 may be located on the appendage strap 12, for example, as part of the onboard control unit 40, and may output a notification in response to an actuation state of the artificial muscles 101 of the appendage pressurization device 10 or indication of a change in the actuation state of the one or more artificial muscles 101 of the appendage pressurization device 10. Moreover, the display device 42 may be a touchscreen that, in addition to providing optical information, detects the presence and location of a tactile input upon a surface of or adjacent to the display device 42. Accordingly, the display device 42 may include the operating device 46 and receive mechanical input directly upon the optical output provided by the display device 42. For example, the user may be able to specify a desired pressure value.

In some embodiments, the actuation system 400 includes network interface hardware 44 for communicatively coupling the actuation system 400 to a portable device 70 via a network 60. The portable device 70 may include, without limitation, a smartphone, a tablet, a personal media player, or any other electric device that includes wireless communication functionality. It is to be appreciated that, when provided, the portable device 70 may serve to provide user commands to the controller 50, instead of the operating device 46. As such, a user may be able to control or set a program for controlling the artificial muscles 101 of the appendage pressurization device 10 utilizing the controls of the operating device 46. Thus, the artificial muscles 101 of the appendage pressurization device 10 may be controlled remotely via the portable device 70 wirelessly communicating with the controller 50 via the network 60. For example, the user may be able to specify a desired pressure value. The portable device 70 may also receive and display pressure readings from one or more pressure sensors 80 associated with one or more of the artificial muscles 101.

Figure 11:
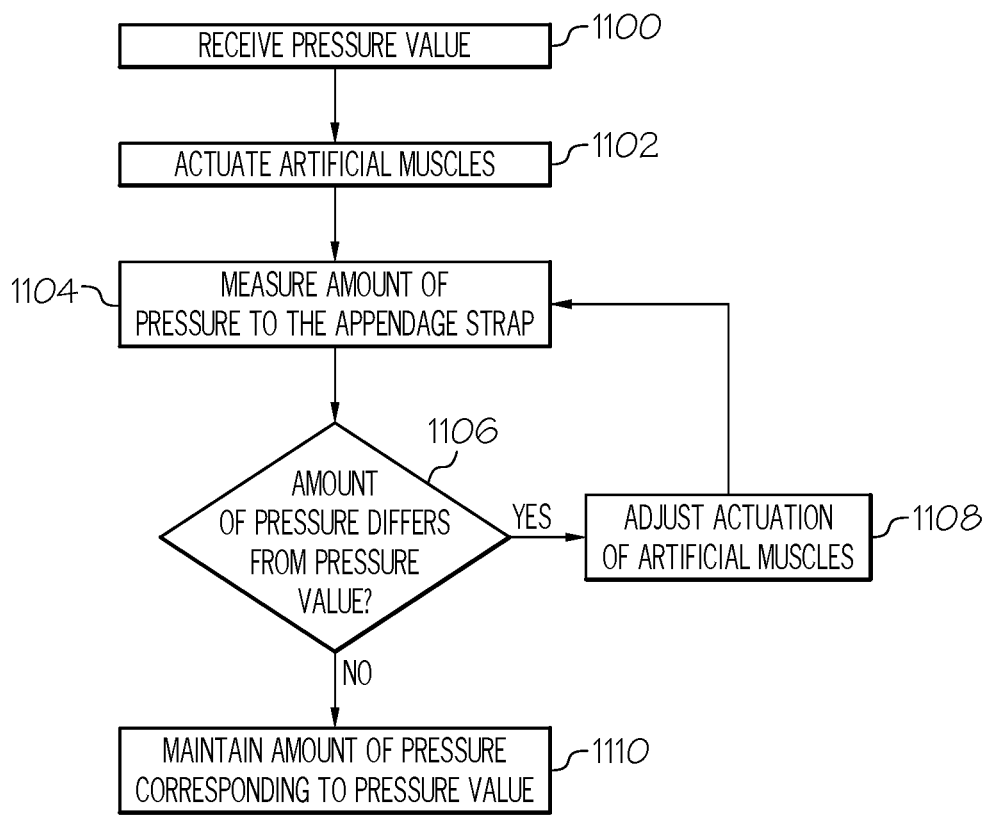
FIG. 11 schematically depicts a flowchart for maintaining a consistent pressure applied by the appendage pressurization device, according to one or more embodiments shown and described herein.

Referring now to FIG. 11, a flowchart depicts an exemplary method for the appendage pressurization device to apply a constant pressure through appendage straps to a user wearing a brace. At block 1100, a pressure value may be received from a pressure sensor or any other suitable device. For example, a user wanting to maintain a constant pressure applied by the appendage straps waits as the pressure sensor measures the current exerted by the appendage straps. At block 1102, one or more artificial muscles may be actuated such that the appendage pressurization device applies pressure through the appendage straps. Continuing with this example, the user waits as the artificial muscles actuate, which increases pressure exerted by the appendage straps. At block 1104, one or more pressure sensors may measure an amount of pressure being applied to a user via the appendage straps of the appendage pressurization device. Continuing with this example, after the artificial muscles have actuated and the appendage straps exert the proper pressure to keep the brace on the appendage, updated pressure measurements may be taken. Specifically, the pressure may be checked to see if the appendage straps have become too tight or too loose.

At block 1106, a determination may be made as to whether the amount of pressure applied by the appendage pressurization device differs from the received pressure value, which may be an updated pressure value. Continuing with this example, the user wants to maintain a constant pressure applied by the appendage straps and thus waits as the pressure sensor compares the current exerted by the appendage straps to obtain an updated pressure value.

If the pressure measured by the pressure sensor(s) differs from the received pressure value, then at block 1108 the actuation of the artificial muscles may be adjusted to, in turn, increase/decrease the pressure exerted by the appendage pressurization device to then match the received pressure value. In some embodiments, there may be a threshold amount of difference to allow for small variations between the received pressure value and the measured pressure value. Continuing with this example, the user holds their appendage still as the muscles are actuated to increase or decrease the pressure from the appendage straps.

Alternatively, if at block 1106 the pressure measured by the pressure sensor(s) matches the received pressure value, then at block 1110 the pressure amount is maintained to correspond to the received pressure value such that the user does not experience any additional loosening or tightening of the appendage straps based upon further actuation of the artificial muscles. An updated pressure value may be received at any time, which would correspond to restarting at block 1100 with the updated pressure value.

It should now be understood that embodiments described herein are directed to appendage pressurization devices that include one or more artificial muscles disposed in an appendage strap and communicatively coupled to a controller. Actuation of the one or more artificial muscles of the appendage pressurization device applies a consistent pressure to hold an appendage brace with constant pressure to the appendage of a user, as measured by a pressure sensor. The pressure sensor, communicatively coupled to the controller, outputs a current pressure value to the controller.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. An appendage pressurization device comprising:
   an appendage strap;
   a plurality of artificial muscles disposed in the appendage strap and communicatively coupled to a controller, wherein each of the plurality of artificial muscles comprise:
      a housing comprising an electrode region and an expandable fluid region;
      a dielectric fluid housed within the housing;
      an electrode pair positioned in the electrode region of the housing, the electrode pair comprising a first electrode fixed to a first surface of the housing and a second electrode fixed to a second surface of the housing, wherein the electrode pair is actuatable between a non-actuated state and an actuated state such that actuation from the non-actuated state to the actuated state directs the dielectric fluid into the expandable fluid region, expanding the expandable fluid region; and
   a pressure sensor communicatively coupled to the controller, wherein the pressure sensor is configured to output a current pressure value to the controller and actuation of the electrode pair is based on the current pressure value;
   wherein each of the plurality of artificial muscles is independently actuatable between the non-actuated state and the actuated state.

2. The appendage pressurization device of claim 1, wherein:
   the first electrode and the second electrode each comprise two or more tab portions and two or more bridge portions;
   each of the two or more bridge portions interconnects adjacent tab portions; and
   either of the first electrode or the second electrode comprises a central opening positioned between the two or more tab portions and encircling the expandable fluid region.

3. The appendage pressurization device of claim 2, wherein the two or more tab portions of the first electrode and the second electrode each include two pairs of tab portions, and the two or more bridge portions of the first electrode and the second electrode each include two pairs of bridge portions, each tab portion diametrically opposing an opposite one of the tab portions.

4. The appendage pressurization device of claim 2, wherein:
   when the electrode pair is in the non-actuated state, the first electrode and the second electrode are non-parallel to one another; and
   when the electrode pair is in the actuated state, the first electrode and the second electrode are parallel to one another, such that the first electrode and the second electrode are configured to zipper toward one another and toward the central opening when actuated from the non-actuated state to the actuated state.

5. The appendage pressurization device of claim 1, wherein the controller is configured to:
   receive the current pressure value from the pressure sensor;
   output an updated pressure value to the plurality of artificial muscles; and
   modify actuation of at least one of the plurality of artificial muscles based upon the updated pressure value.

6. The appendage pressurization device of claim 5, wherein a consistent amount of pressure at an inner layer of the appendage strap is maintained based upon a feedback loop maintained by the controller in coordination with the pressure sensor.

7. The appendage pressurization device of claim 1, wherein the plurality of artificial muscles are arranged in a stack such that the expandable fluid region of each artificial muscle are coaxially aligned with one another.

8. The appendage pressurization device of claim 7, further comprising a plurality of artificial muscle stacks.

9. The appendage pressurization device of claim 1, wherein the housing of each of the plurality of artificial muscles comprises a first film layer and a second film layer partially sealed to one another to define a sealed portion of the housing, the housing further comprising an unsealed portion surrounded by the sealed portion, wherein the electrode region and the expandable fluid region of the housing are disposed in the unsealed portion.

10. The appendage pressurization device of claim 1, further comprising a first electrical insulator layer fixed to an inner surface of the first electrode opposite the first surface of the housing and a second electrical insulator layer fixed to an inner surface of the second electrode opposite the second surface of the housing, wherein the first electrical insulator layer and the second electrical insulator layer each includes an adhesive surface and an opposite non-sealable surface.

11. The appendage pressurization device of claim 1, wherein the plurality of artificial muscles are arranged in a single layer.

12. The appendage pressurization device of claim 1, wherein the appendage strap comprises a first appendage strap and the appendage pressurization device further comprises a second appendage strap comprising one or more artificial muscles.

13. An appendage pressurization device comprising:
   an appendage brace;
   an appendage strap coupled to the appendage brace;
   a plurality of artificial muscles disposed in the appendage strap and communicatively coupled to a controller, wherein each artificial muscle comprises:
      a housing comprising an electrode region and an expandable fluid region;
      a dielectric fluid housed within the housing; and
      an electrode pair positioned in the electrode region of the housing, the electrode pair comprising a first electrode fixed to a first surface of the housing and a second electrode fixed to a second surface of the housing, wherein the electrode pair is actuatable between a non-actuated state and an actuated state such that actuation from the non-actuated state to the actuated state directs the dielectric fluid into the expandable fluid region, thereby expanding the expandable fluid region;
   a pressure sensor communicatively coupled to the controller, wherein the pressure sensor is configured to output a current pressure value to the controller; and
   the controller, wherein the controller is configured to:
      receive the current pressure value from one the pressure sensor;
      output an updated pressure value to artificial muscles, wherein a consistent amount of pressure at an inner layer of the appendage strap is maintained based upon a feedback loop maintained by the controller in coordination with the pressure sensor; and
      modify actuation of the plurality of artificial muscles based upon the updated pressure value;
   wherein each of the plurality of artificial muscles is independently actuatable between the non-actuated state and the actuated state.

14. The appendage pressurization device of claim 13, wherein:
   the first electrode and the second electrode each comprise two or more tab portions and two or more bridge portions;
   each of the two or more bridge portions interconnects adjacent tab portions; and
   either the first electrode or the second electrode comprises a central opening positioned between the two or more tab portions and encircling the expandable fluid region.

15. The appendage pressurization device of claim 14, wherein the two or more tab portions of the first electrode and the second electrode each include two pairs of tab portions, and the two or more bridge portions of the first electrode and the second electrode each include two pairs of bridge portions, each tab portion diametrically opposing an opposite one of the tab portions.

16. A method for actuating an appendage pressurization device, the method comprising:
   generating a voltage using a power supply electrically coupled to an electrode pair of each of a plurality of artificial muscles, the plurality of artificial muscles being disposed in an appendage strap, wherein:
      each of the plurality of artificial muscles comprises a housing having an electrode region and an expandable fluid region;
      the electrode pair is positioned in the electrode region of the housing;
      the electrode pair comprises a first electrode fixed to a first surface of the housing and a second electrode fixed to a second surface of the housing, and a dielectric fluid is housed within the housing; and
      a pressure sensor is affixed to the housing and communicatively coupled to a controller;
   applying the voltage to the electrode pair of each of the plurality of artificial muscles, thereby actuating the electrode pair from a non-actuated state to an actuated state such that the dielectric fluid is directed into the expandable fluid region of the housing and expands the expandable fluid region, thereby applying pressure to an inner layer of the appendage strap;
   outputting, via the pressure sensor, a pressure value to the controller;
   receiving, from the controller, an updated pressure value at the plurality of artificial muscles to maintain a consistent amount of pressure at the inner layer of the appendage strap based upon the pressure value; and
   adjusting the actuation of the plurality of artificial muscles to maintain the consistent amount of pressure at the inner layer of the appendage strap;
   wherein each of the plurality of artificial muscles is independently actuatable between the non-actuated state and the actuated state.

17. The method of claim 16, further comprising:
   receiving a current pressure value from the pressure sensor;
   outputting a second updated pressure value to the plurality of artificial muscles; and
   modifying actuation of the plurality of artificial muscles based upon the second updated pressure value to maintain the consistent amount of pressure at the inner layer of the appendage strap.

18. The method of claim 16, further comprising adjusting the actuation of each of the plurality of artificial muscles to maintain the consistent amount of pressure at the inner layer of the appendage strap.

19. The method of claim 16, wherein the appendage strap is coupled to an appendage brace.

* * * * *